United States Patent
Edelman et al.

(10) Patent No.: US 11,779,687 B2
(45) Date of Patent: Oct. 10, 2023

(54) BREASTMILK PUMP

(71) Applicant: Annabella Tech Ltd., Ashdod (IL)

(72) Inventors: Ron Edelman, Ashdod (IL); Semion Waldberg, Ramat Hasharon (IL); Maria Waldberg, Ramat Hasharon (IL)

(73) Assignee: Annabella Tech Ltd., Ashdod (IL)

( * ) Notice: Subject to any disclaimer, the term of this patent is extended or adjusted under 35 U.S.C. 154(b) by 456 days.

(21) Appl. No.: 16/465,673

(22) PCT Filed: Jun. 15, 2018

(86) PCT No.: PCT/IL2018/050667
§ 371 (c)(1),
(2) Date: May 31, 2019

(87) PCT Pub. No.: WO2018/229782
PCT Pub. Date: Dec. 20, 2018

(65) Prior Publication Data
US 2020/0016307 A1     Jan. 16, 2020

Related U.S. Application Data

(60) Provisional application No. 62/519,897, filed on Jun. 15, 2017.

(51) Int. Cl.
*A61M 1/06* (2006.01)

(52) U.S. Cl.
CPC .............. *A61M 1/06* (2013.01); *A61M 1/064* (2014.02); *A61M 1/06935* (2021.05); *A61M 2205/52* (2013.01); *A61M 2209/088* (2013.01)

(58) Field of Classification Search
CPC .......... A61M 1/007; A61M 2210/1007; A61M 1/06; A61M 1/062; A61M 1/064; A61M 1/066; A61M 1/068; A61M 1/0697; A61M 1/067; A61M 1/069; A61M 1/0693; A61M 1/06935; A61B 2018/00333; A61J 13/00; A61H 15/0078; A61H 7/008; A61H 2205/082
See application file for complete search history.

(56) References Cited

U.S. PATENT DOCUMENTS

| | | | |
|---|---|---|---|
| 4,772,262 A | 9/1988 | Grant et al. | |
| 6,004,288 A | * 12/1999 | Hochstedler | ............ A61M 1/06 417/474 |
| 6,383,163 B1 | 5/2002 | Kelly et al. | |

(Continued)

FOREIGN PATENT DOCUMENTS

| | | |
|---|---|---|
| CA | 2240268 A1 | 12/1999 |
| CN | 101687068 A | 3/2010 |

(Continued)

OTHER PUBLICATIONS

International Search Report and Written Opinion from International Application No. PCT/IL201/050667 dated Sep. 26, 2018.

(Continued)

*Primary Examiner* — Kevin C Sirmons
*Assistant Examiner* — William R Frehe
(74) *Attorney, Agent, or Firm* — Dorsey & Whitney LLP

(57) ABSTRACT

The present invention relates to breastmilk pumps imitating the suckling mechanism of a baby's mouth.

18 Claims, 17 Drawing Sheets

(56) References Cited

U.S. PATENT DOCUMENTS

| | | | |
|---|---|---|---|
| 6,676,610 B2 | 1/2004 | Morton et al. | |
| 8,052,635 B1 | 11/2011 | Kelly et al. | |
| 9,050,404 B2 | 6/2015 | Silver et al. | |
| 2005/0234400 A1 | 10/2005 | Onuki et al. | |
| 2005/0256449 A1 | 11/2005 | Tashiro | |
| 2006/0178601 A1 | 8/2006 | Wang et al. | |
| 2008/0045887 A1 | 2/2008 | Larsson et al. | |
| 2008/0177224 A1 | 7/2008 | Kelly et al. | |
| 2010/0130921 A1* | 5/2010 | Kobayashi | A61M 1/06 604/74 |
| 2011/0270162 A1 | 11/2011 | Guo | |
| 2014/0330200 A1* | 11/2014 | Scheidegger | A61M 1/064 604/74 |
| 2015/0065994 A1 | 3/2015 | Fridman et al. | |
| 2016/0058928 A1 | 3/2016 | Nowroozi et al. | |
| 2016/0206794 A1 | 7/2016 | Makower et al. | |
| 2016/0220745 A1 | 8/2016 | Guthrie et al. | |
| 2016/0325031 A1 | 11/2016 | Miller et al. | |
| 2017/0072118 A1* | 3/2017 | Makower | A61M 1/067 |
| 2018/0326130 A1* | 11/2018 | Thompson | A61M 1/06 |
| 2021/0268159 A1* | 9/2021 | Schwarz | A61M 1/06 |
| 2021/0361837 A1* | 11/2021 | Bijoor | A61M 1/0693 |

FOREIGN PATENT DOCUMENTS

| | | | |
|---|---|---|---|
| CN | 108478407 A * | 9/2018 | |
| EP | 2604300 A1 | 6/2013 | |
| EP | 3171907 A4 | 5/2018 | |
| JP | 2007089903 A | 4/2007 | |
| TW | M445988 U | 2/2013 | |
| WO | 2011137994 A1 | 11/2011 | |
| WO | 2016044802 A1 | 3/2016 | |
| WO | WO-2021186006 A1 * | 9/2021 | A61M 1/064 |

OTHER PUBLICATIONS

U.S. Appl. No. 62/519,897, filed Jun. 15, 2017.

Alekseev, N P. et al., "Compression stimuli increase the efficacy of breast pump function", European Journal of Obstetrics & Gynecology and Reproductive Biology; vol. 77, 1998, pp. 131-139.

* cited by examiner

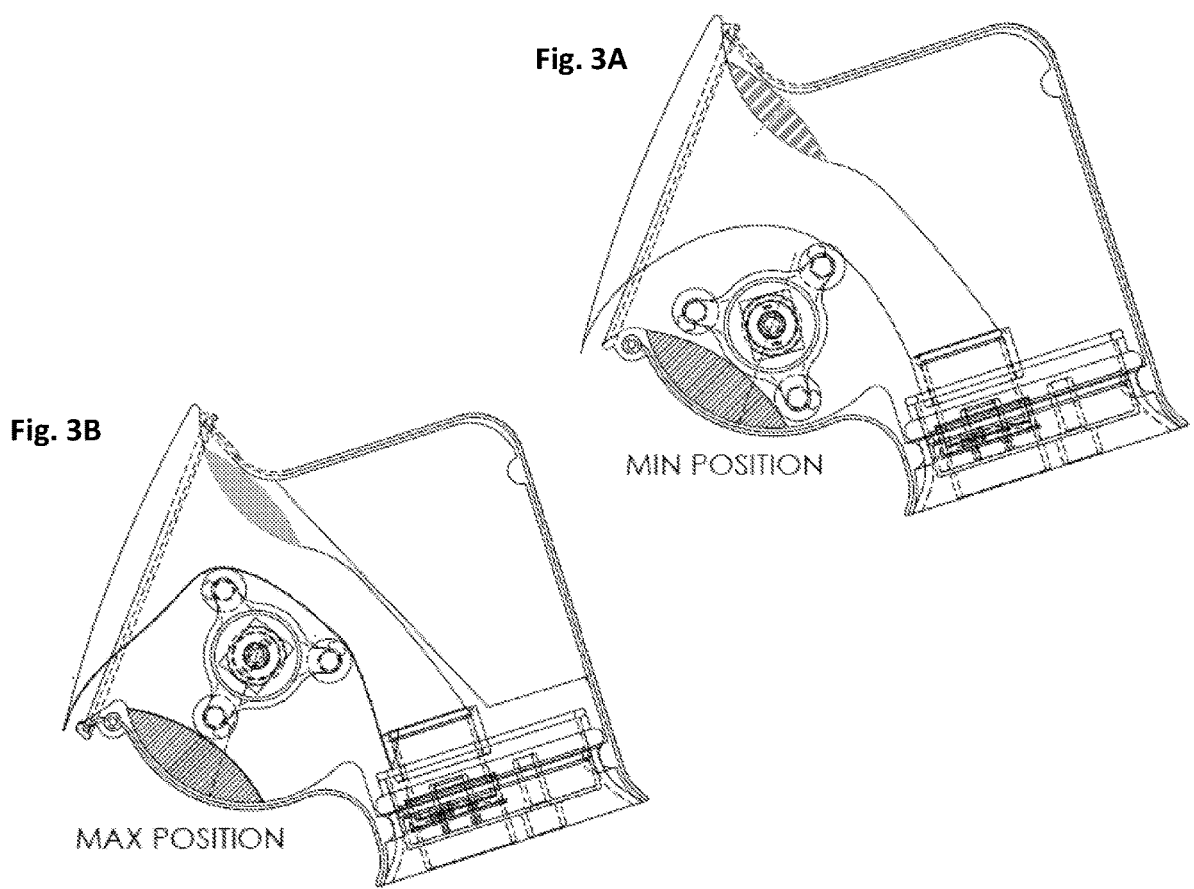
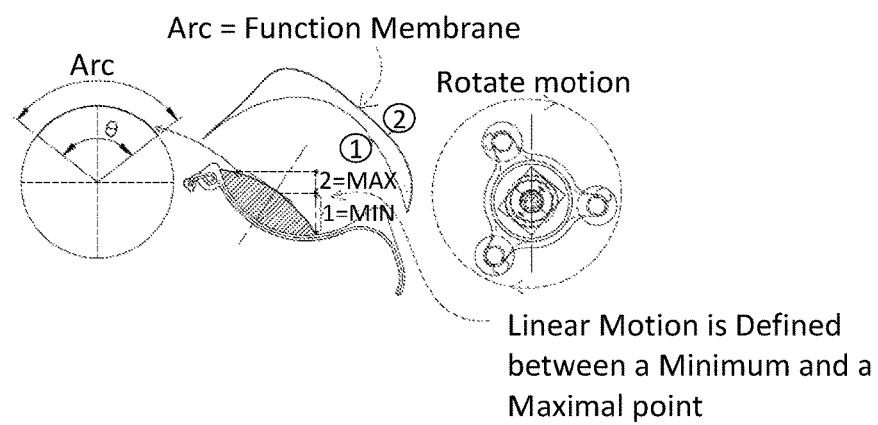
Fig. 3C

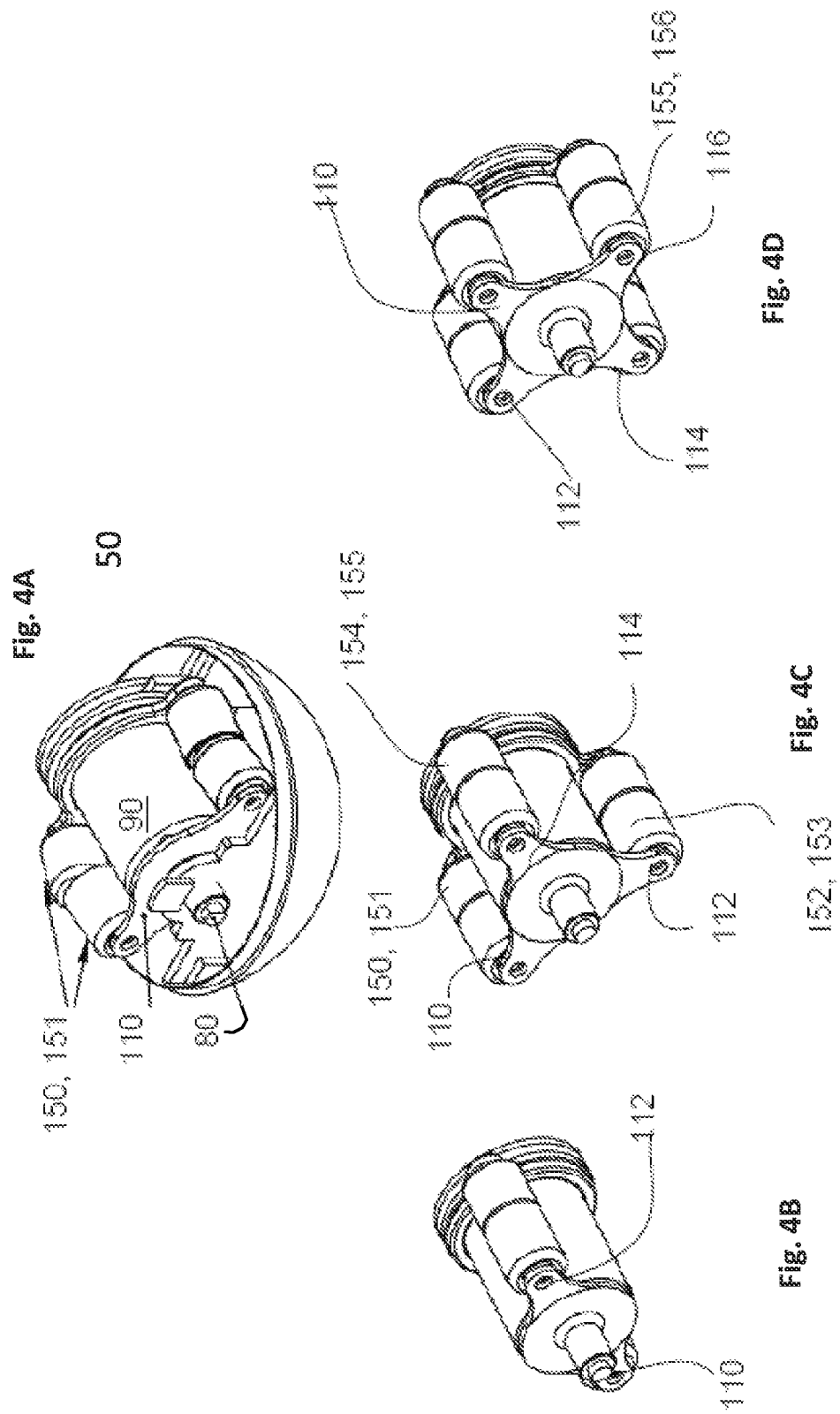

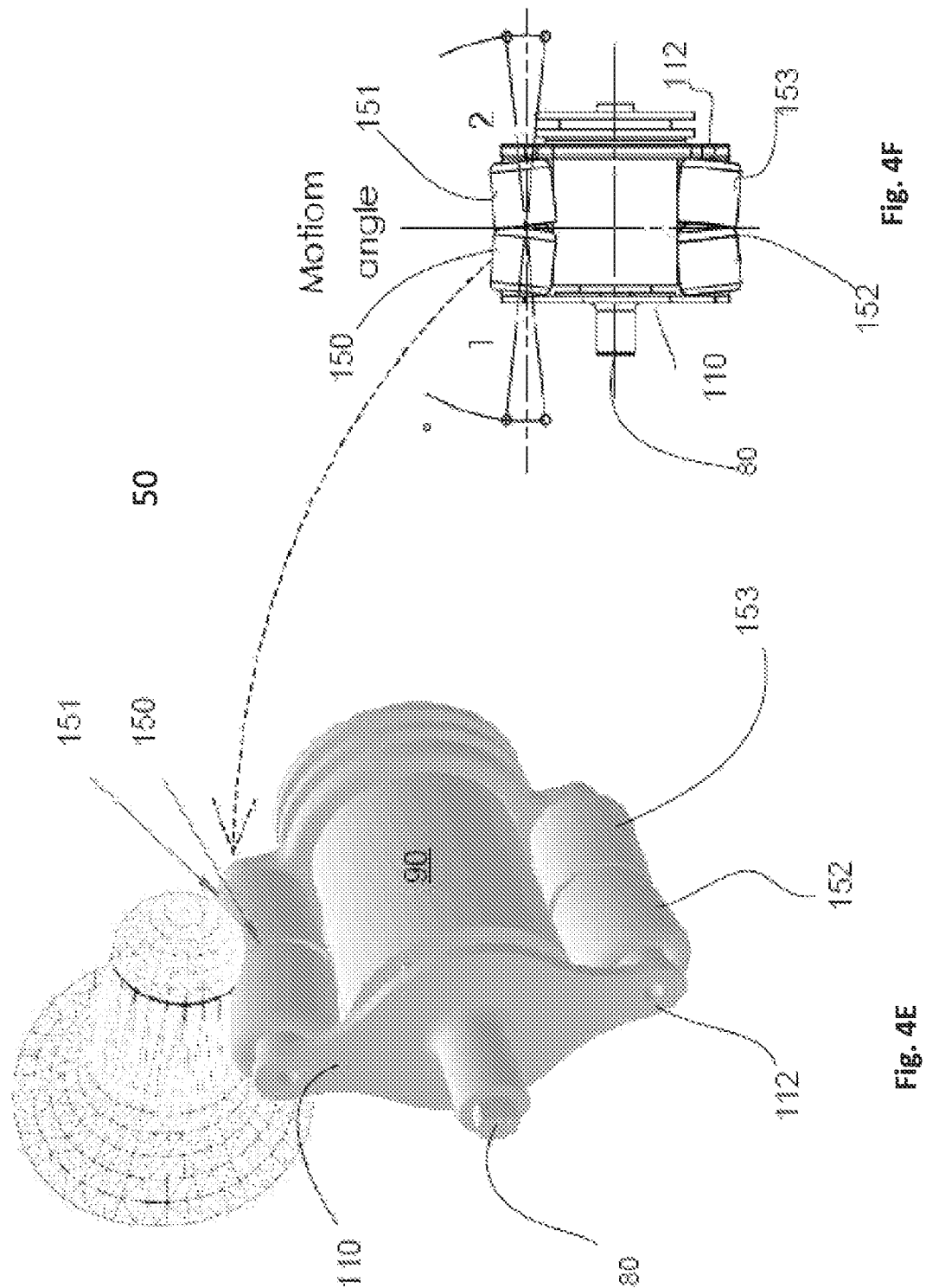

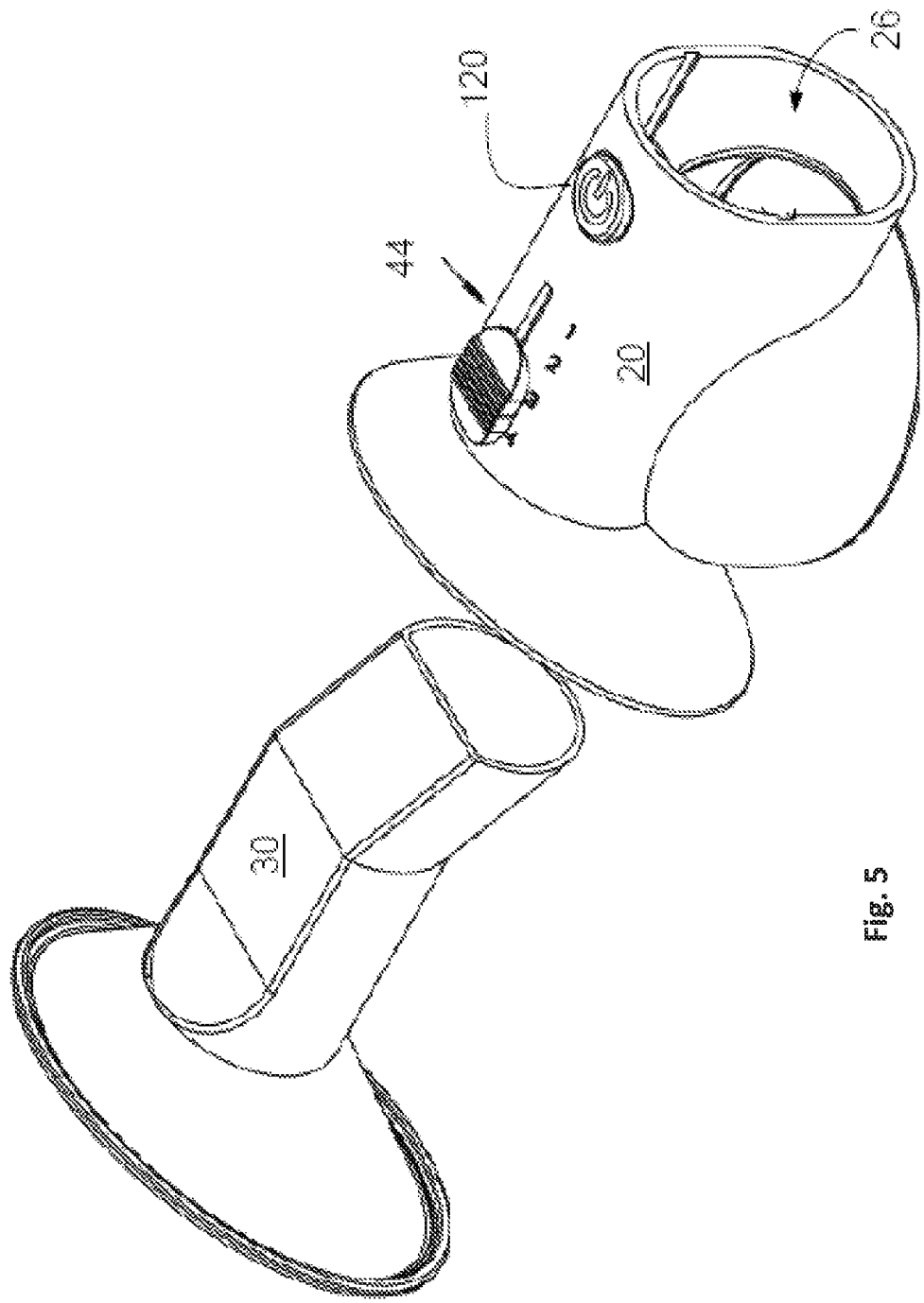

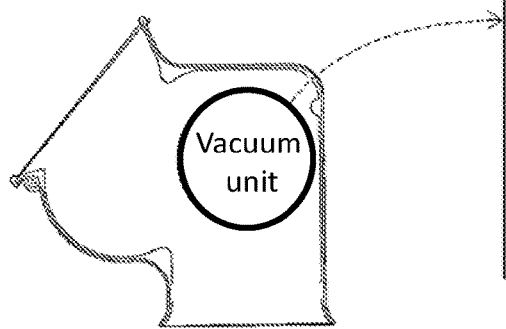
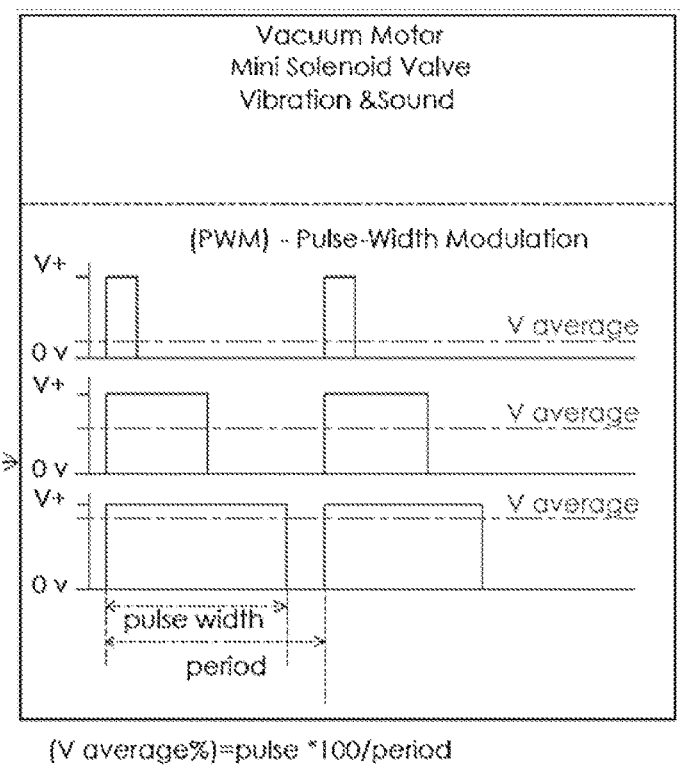
Fig. 7A
Fig. 7B

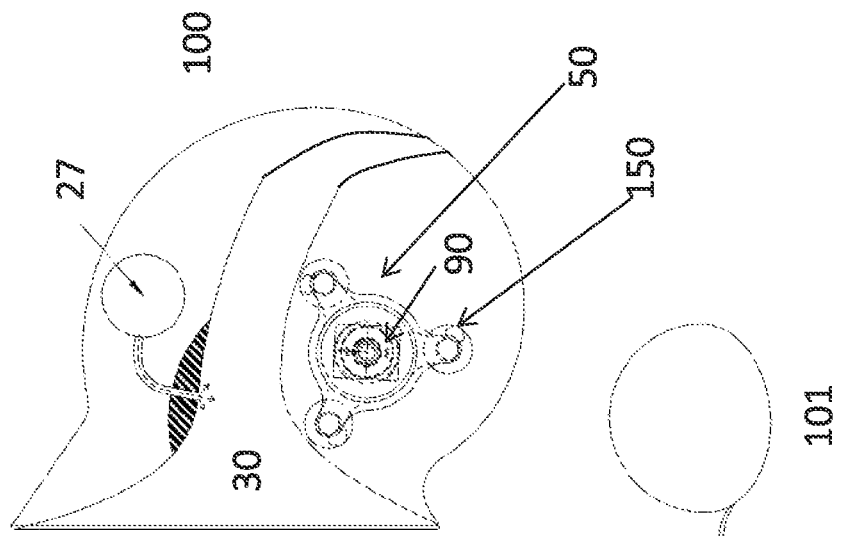
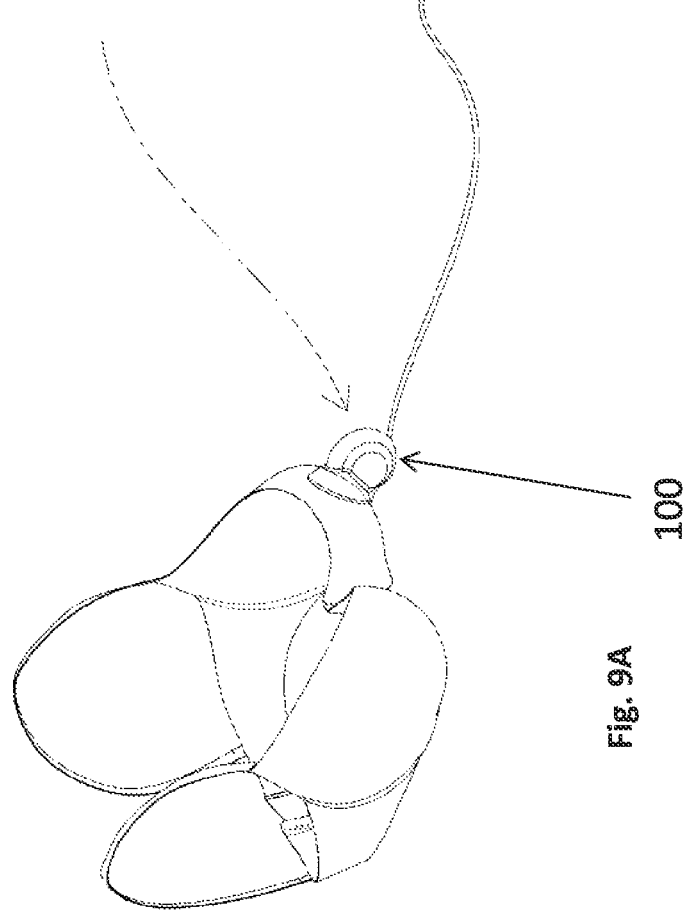

BREASTMILK PUMP

FIELD OF INVENTION

The present invention relates to a breastmilk pump for collecting breastmilk, more particularly a breastmilk pump that is designed to improve milk production and reduce damage and pain to the mother by imitating the suckling of a baby and a baby's mouth including a tongue-imitating mechanism designed to mimic a baby's tongue movement during breastfeeding.

BACKGROUND

Pumping breastmilk and storing it for short periods of time (of up to 6 months) is highly beneficial since it allows breastfeeding mothers to be independent by enabling feeding the baby with breastmilk even in their absence by a third party, and by providing breastmilk to mothers that cannot breast feed for any reason. Therefore, different breastmilk pumps were developed to enable pumping breastmilk, all of which use pulsating negative pressure using a pump, such as a diaphragm pump, that is connected to a collecting container. The negative pressure causes the nipple to aspire breastmilk in a pulsating manner, thereby producing a pumping effect on the areola in which the milk collects and is drawn through the nipple by the negative pressure.

Examples of known breastmilk pumps are described, e.g., in U.S. Pat. No. 6,004,288, US 2016/058928, US 2014/330200, US 2005/234400, US 2016/206794 and US 2011/270162.

However, current breastmilk pumps suffer from many disadvantages, such as noisiness caused due to the pulsating negative pressure. Another disadvantage is the fact that the described suction and extension of the nipple produces friction between the latter and the pump (i.e. the funnel of the pump), which may cause irritations and/or wound the nipple.

Other major disadvantages of current breastmilk pumps are their inability to pump all the milk in the breast, which may cause the breast to produce less milk, and their diverged efficiency compared to natural breast feeding, which may force the mother to perform multiple unnecessary pumping attempts. The disadvantages of current breast pumps are usually since they are not physiologically compatible with the human breast: a strong vacuum and a pulsing motion is not enough to help the mother express milk efficiently. In addition, breast pumps today do not have the correct form that is needed to extract milk from the breast. Therefore, they are not able to extract milk as efficiently as a baby or hand expression would.

SUMMARY

On account of the aforementioned disadvantages and of the fact that in known breastmilk pumps, the pumping process substantially differs from the natural sucking of a baby, many women find breastmilk pumping displeasing, painful and/or irritating and therefore refrain therefrom. Accordingly, the present invention provides a breastmilk pump 10 that does not suffer from the aforementioned disadvantages and more particularly is gentle to the breast and nipple during use, and better imitates the milk suction mechanism of a baby. It should be noted that the basic assumption that milk comes out of the breast due to strong vacuum is not accurate. In fact, it has been found that milk is extracted due to high oxytocin levels in the body, which is triggered by a baby's suckling motion.

In one aspect, the present invention provides a breastmilk pump 10 for pumping breastmilk from the breast of a mother, comprising: (a) a body 20; (b) a funnel 30 having a distal end 26 and a proximal end 24; (c) a vacuum unit; (d) a lower manipulating mechanism 50; (e) at least one sensor; and (f) a microcomputer comprising a processor coupled to a memory and interfaces, wherein the memory contains instructions that, when executed by the processor, cause the processor to activate/deactivate said vacuum unit and said lower manipulating mechanism 50 in a cyclic manner and optionally change the vacuum intensity, lower manipulating mechanism 50 speed and position thereof, based on (i) data (continuously) received from said at least one sensor; and (ii) predefined parameters stored in said memory, wherein: (i) said funnel 30 is designed to fit into said body 20; (ii) said funnel's proximal end 24 has a conic shape designed to embrace a breast and a nipple, and is made of a flexible material; (iii) said vacuum unit is associated with said funnel 30 and designed to generate negative pressure (vacuum) in the pump 10 and between the funnel 30 and the breast; (iv) said lower manipulating mechanism 50 is a tongue-imitating mechanism designed to mimic a baby's tongue movement during breastfeeding; and said at least one sensor is designed for sensing/measuring at least one of: location of the lower manipulating mechanism 50, rotation (speed and number) of the lower manipulating mechanism 50, negative pressure intensity, distance between the funnel and the breast; milk flow; and the location of the upper movable element 42, or any combination thereof.

In another aspect, the present invention relates to a breastmilk pump system for pumping breastmilk from the breast of a mother, comprising: (1) a minimal breastmilk pump unit 100 designed to be attached to the breast and nipple, said unit 100 comprising: (a) a body 20; (b) a funnel 30 having a distal end 26 and a proximal end 24; and (c) a lower manipulating mechanism 50; wherein: (i) said funnel 30 is designed to fit into said body 20; (ii) said funnel's proximal end 24 has a conic shape designed to embrace a nipple, and is made of a flexible material; and (iii) said lower manipulating mechanism 50 is a tongue-imitating mechanism designed to mimic a baby's tongue movement over the breast/nipple during breastfeeding; (2) a remote unit 101 for collecting the pumped breastmilk, said unit 101 comprising: (a) a detachable breastmilk container; and a vacuum unit associated with said funnel 30 and designed to generate negative pressure (vacuum) in the pump 10 and between the funnel 30 and the breast; (iii) at least one sensor designed for sensing/measuring at least one of: location of the lower manipulating mechanism 50, rotation (speed and number) of the lower manipulating mechanism 50, negative pressure intensity, distance between the funnel and the breast; milk flow; and the location of the upper movable element 42, or any combination thereof; and; (iv) a microcomputer comprising a processor coupled to a memory and interfaces, wherein the memory contains instructions that, when executed by the processor, cause the processor to activate/deactivate said vacuum unit and said lower manipulating mechanism 50 in a cyclic manner, and optionally change the vacuum intensity, lower manipulating mechanism 50 speed and position thereof, based on (i) data (continuously) received from said at least one sensor; and (ii) predefined parameters stored in said memory, wherein said funnel 30 is fluidly connected to said breastmilk container.

BRIEF DESCRIPTION OF THE DRAWINGS

FIG. 1A is a 3-dimensional view;

FIG. 1B is an upper view showing the activation buttons;
FIG. 1C is a side cross view showing the main components; and FIG. 1D is a 3-dimensional cross view showing the main components.

FIG. 2A is a side cross view; FIGS. 2B-2C illustrate how the inner motor rotates to create a tongue-like motion.

FIGS. 3A-3C are illustrations of a dynamic breastmilk pump according to the invention: FIG. 3A shows the minimum location of the roller; FIG. 3B shows the maximum location of the roller; and FIG. 3C illustrates how the movement of the roller imitates a tongue-like motion.

FIGS. 4A-4F illustrate the structure of the roller: FIGS. 4A-4D show possible configurations of the roller; and FIGS. 4E-4F illustrate the effect of the roller's structure on the nipple.

FIG. 5 illustrates the assembly of the funnel in the body of a breastmilk pump of the invention.

FIGS. 7A-7B illustrate the role of the vacuum unit in the breastmilk pump of the invention.

FIGS. 9A-9B illustrate a system comprising a breastmilk pump according to some embodiments of the invention.

DETAILED DESCRIPTION

Figure 1A:
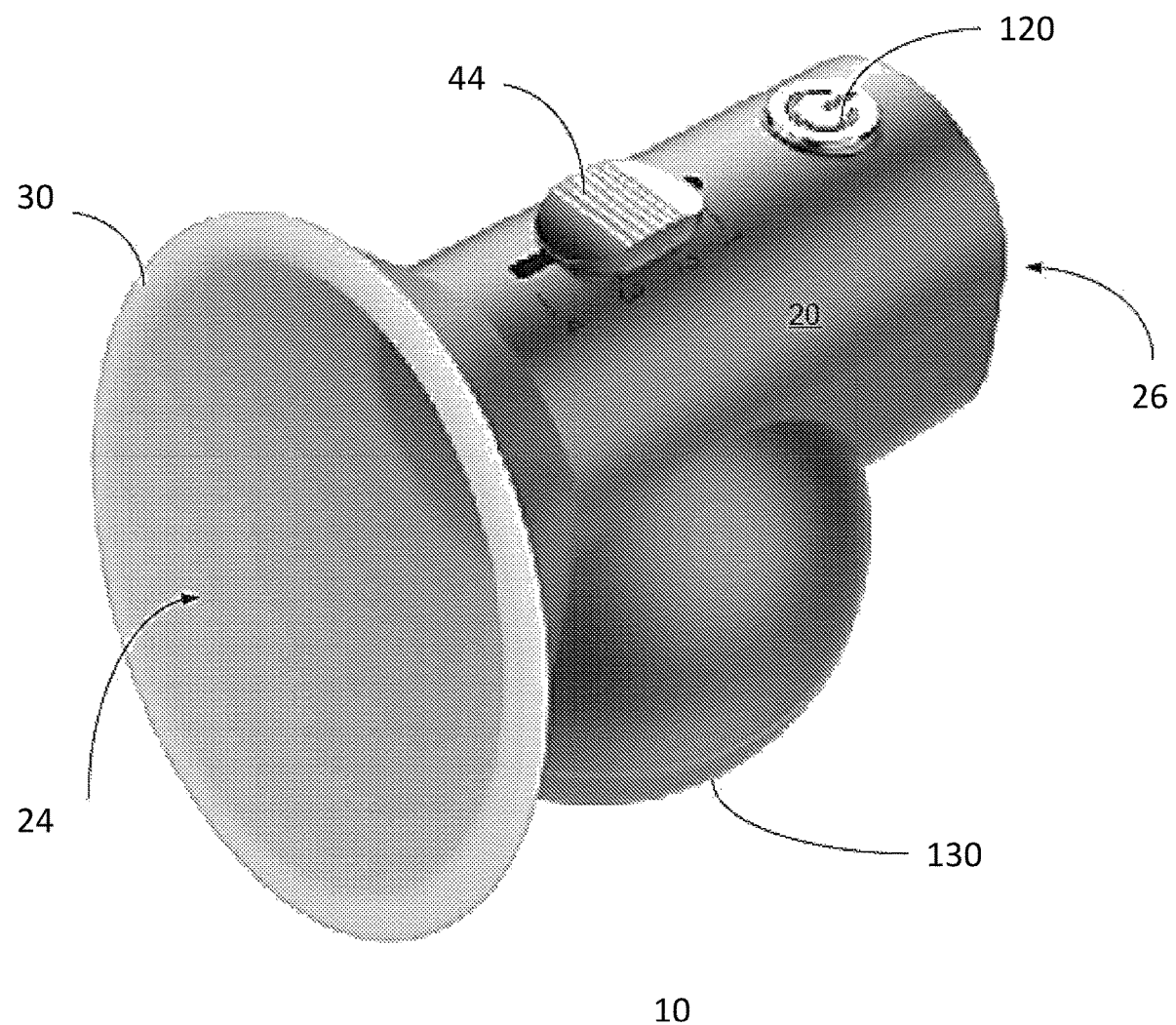
FIGS. 1A-1D are illustrations of a breastmilk pump according to the invention.

The present invention is aimed at providing an efficient breastmilk pump that is both efficient, quiet, light weighted, portable and cause minimal discomfort, pain and damage to the nipple and breast of the mother.

Accordingly, the present invention provides a breastmilk pump 10 for pumping breastmilk, comprising: (a) a body 20; (b) a funnel 30 having a distal end 26 and a proximal end 24; (c) a vacuum unit; and (d) a lower manipulating mechanism 50; wherein: (i) said funnel 30 is designed to fit into said body 20; (ii) said funnel's proximal end 24 has a conic shape designed to embrace a nipple, and is made of a flexible material defining a flexible portion 21 (FIG. 1C) extending at least at a lower portion of the funnel 30; and (iii) said lower manipulating mechanism 50 is a tongue-imitating mechanism designed to mimic a baby's tongue movement during breastfeeding.

In one aspect, the present invention provides a breastmilk pump 10 for pumping breastmilk from the breast of a mother, comprising: (a) a body 20; (b) a funnel 30 having a distal end 26 and a proximal end 24; (c) a vacuum unit; (d) a lower manipulating mechanism 50; (e) at least one sensor; and (f) a microcomputer comprising a processor coupled to a memory and interfaces, wherein the memory contains instructions that, when executed by the processor, cause the processor to activate/deactivate said vacuum unit and said lower manipulating mechanism 50 in a cyclic manner, and optionally change the vacuum intensity, lower manipulating mechanism 50 speed and position thereof, based on (i) data (continuously) received from said at least one sensor; and (ii) predefined parameters stored in said memory, wherein: (i) said funnel 30 is designed to fit into said body 20; (ii) said funnel's proximal end 24 has a conic shape designed to embrace a nipple, and is made of a flexible material; (iii) said vacuum unit is associated with said funnel 30 and designed to generate negative pressure (vacuum) in the pump 10 and between the funnel 30 and the breast; (iv) said lower manipulating mechanism 50 is a tongue-imitating mechanism designed to mimic a baby's tongue movement during breastfeeding; and said at least one sensor is designed for sensing/measuring at least one of: location of the lower manipulating mechanism 50, rotation (speed and number) of the lower manipulating mechanism 50, negative pressure intensity, distance between the funnel and the breast; milk flow; and the location of the upper movable element 42, or any combination thereof.

In certain embodiments, the breastmilk pump 10 further comprises a breastmilk container for storing the pumped breastmilk, wherein said funnel's distal end 26 is fluidly connected thereto. Said milk chamber/container may be directly connected to the body and constitute part thereof, or may be remotely associated therewith, e.g., via a tube delivering the breastmilk thereto. In certain embodiments, said milk container is removably connected to the funnel 30 and/or the body 20 by any suitable means, such as a coupling device, or a screw mechanism.

In certain embodiments, the breastmilk pump 10 of any one of the embodiments above further comprises a control knob 44 for modifying the shape and/or location of the funnel's upper part to obtain best fit of the breast and nipple, thereby improving milk flow and reducing abrasion of the nipple.

In certain embodiments, the breastmilk pump 10 of any one of the embodiments above further comprises a vacuum intensity control for enabling the user to control the vacuum intensity and/or pulses/cycles.

In certain embodiments, the breastmilk pump 10 of any one of the embodiments above further comprises a lower manipulating mechanism 50 control unit for enabling the user to control and adjust the: (i) location of the lower manipulating mechanism 50; and/or (ii) the rotation speed and/or cycles.

In certain embodiments, the controlling of the different embodiments and functions, all or some, of the breastmilk pump 10 of any one of the embodiments above is conducted wirelessly from a remote controller or a remote computer, such as a smartphone or tablet.

The term "computer" or "microcomputer" as used herein interchangeably, refer to any type of computer that can be instructed to carry out sequences of arithmetic or logical operations automatically via computer programming. The built-in microcomputer of the pump 10 or pump system of the invention reads data from various sensors in the pump 10 of the invention, such as: sensor detecting the position of the lower manipulating mechanism's 50, sensor for measuring/detecting vacuum pressure, etc., and from the different buttons and controls and controllers of the pump 10 or pump system. The built-in microcomputer controls the activity of the different motors, vent valve, screen, and other components of the pump 10 or pump system of the invention. In addition, in certain embodiments, the microcomputer controls the entire pumping process.

Figure 1B:
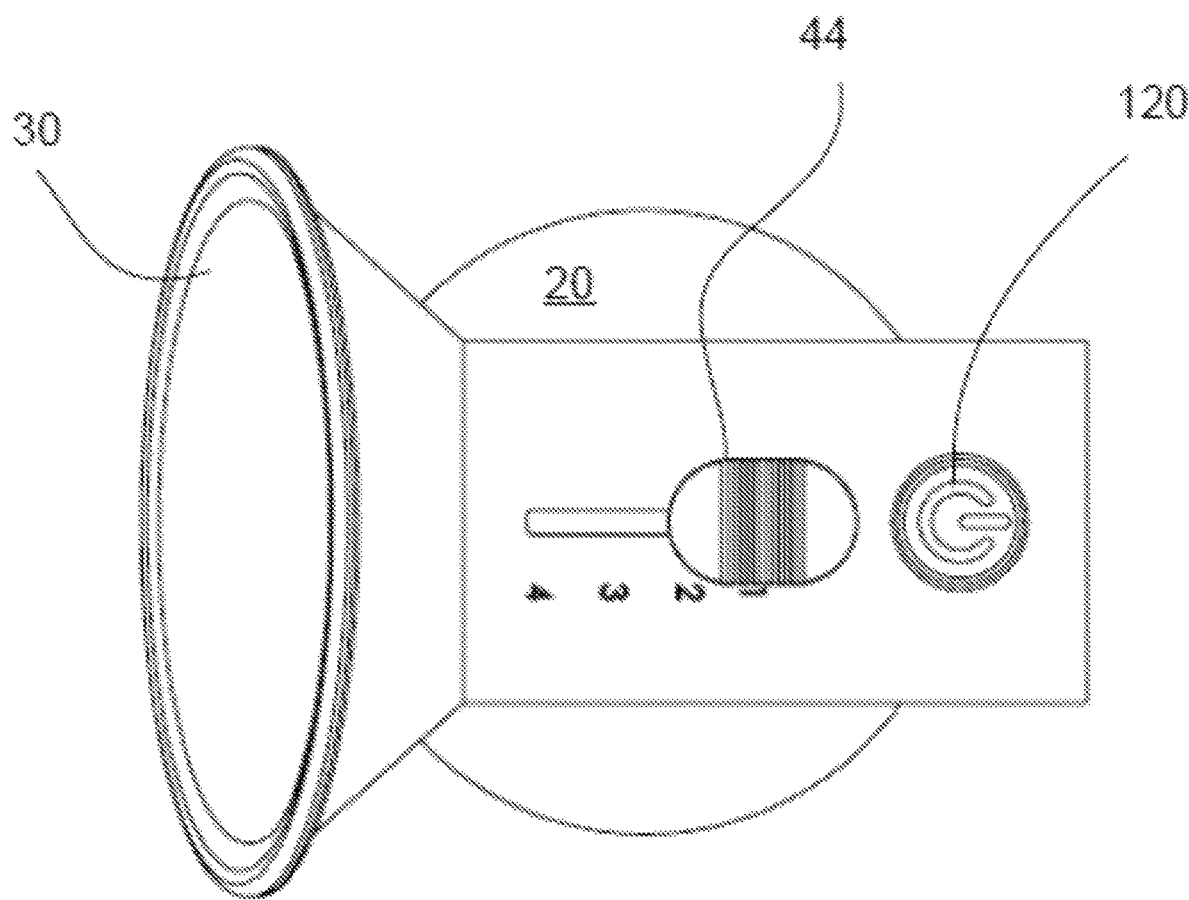
Figure 1C:
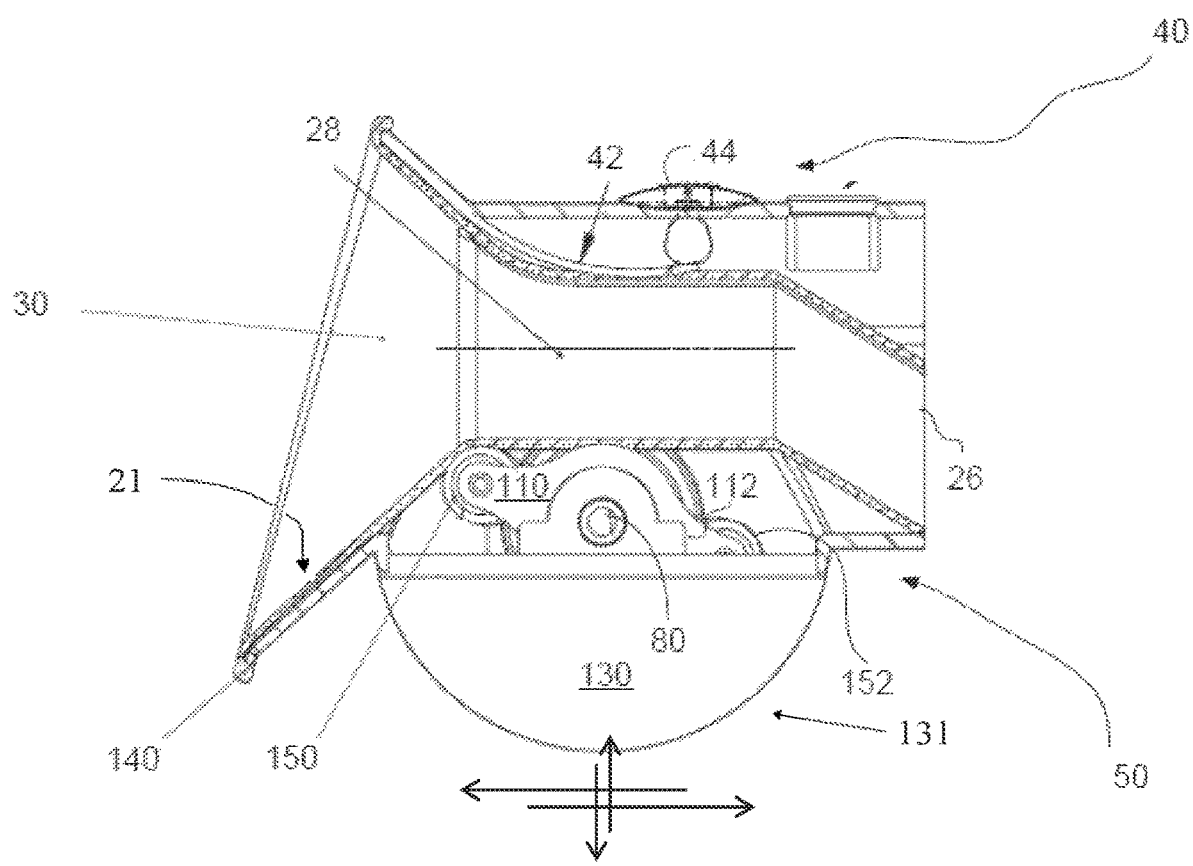
Figure 1D:
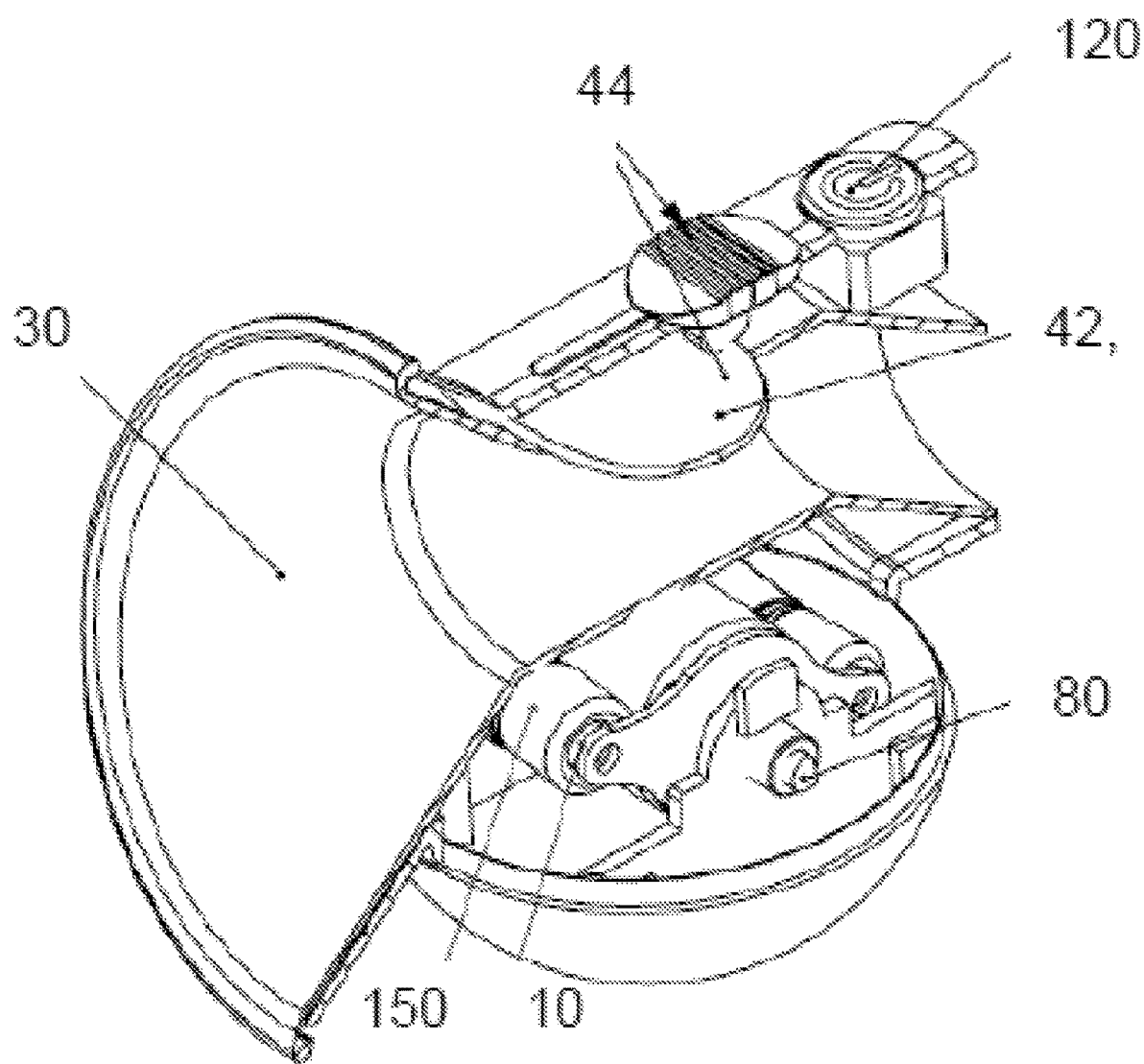

In certain embodiments of the breastmilk pump 10 of any one of the embodiments above, the lower manipulating mechanism 50 is located at a movable base 130 constituting at least part of an adjustment mechanism 131 that is associated with said body 20 and that can move in relation to the body 20, to thereby adjust the location and orientation of the funnel's lower part by moving the tongue-imitating mechanism 50, relative to the nipple within the funnel 30 (see arrows in FIG. 1C). In certain embodiments, the lower manipulating mechanism 50 is located at an affixed lower part of the body 130 that is not movable, and the lower manipulating mechanism 50 is attached to an adjustment mechanism 131 that can move the lower manipulating mechanism 50 in relation to the body 20 in any direction. In certain embodiments, the movement of the lower manipulating mechanism 50 is designed to enable the user to fit the funnel 30 to her nipple for increasing the pumping efficiency and comfort and reduce abrasion. In certain embodiments, the movement of the lower manipulating mechanism 50 is controlled by the microcomputer.

In certain embodiments, the lower manipulating mechanism 50 is located within the lower part of said funnel 30 and can move in any direction in relation to the body 20.

In certain embodiments, the breastmilk pump 10 of any one of the embodiments above, further comprises an electric motor for shifting the location of the lower manipulating mechanism 50 with or without a mechanism to automatically adjust the location and speed of the lower manipulating mechanism 50.

In certain embodiments of the breastmilk pump 10 of any one of the embodiments above, the vacuum unit is a negative pressure pump. In further embodiments, the vacuum unit is designed to generate variable negative pressure/vacuum according to the progress of the pumping process, namely increase or decrease the vacuum generated in order to increase or decrease, respectively, the pumping of the milk as the pumping process progresses.

In certain embodiments of the breastmilk pump 10 of any one of the embodiments above, the vacuum unit is designed to generate vacuum pulses.

In certain embodiments of the breastmilk pump 10 of any one of the embodiments above, the microcomputer: (i) modify the location and/or rotation speed of the lower manipulating mechanism 50; (ii) activates/deactivates said vacuum unit; optionally (iii) the location and/or direction of the upper part of the funnel via the upper movable element 42, for generating pumping sequences that include variable vacuum speed and intensity; and (iv) automatically positions the lower manipulation mechanism 50 and upper movable element 42 to obtain optimal contact and position of the funnel 30 in respect to the nipple/breast for obtaining best vacuum conditions.

In certain embodiments of the breastmilk pump 10 of any one of the embodiments above, the vacuum unit is an open- or a closed-system pump. The term "closed system pump" refers to a system that has a barrier between the motor and the milk collection kit that keeps the milk from entering the air tubing. The term "open system pump" refers to a system that does not have such a barrier, and which can allow some milk particles to enter the air tubing.

In certain embodiments of the breastmilk pump 10 of any one of the embodiments above is able to record or memories a pumping sequence, namely the combination of variable, vacuum, speed and location of lower manipulating mechanism 50, location of the upper movable element 42 as a function of time, to be "replayed" by the user upon demand.

In certain embodiments of the breastmilk pump 10 of any one of the embodiments above, the negative pressure/vacuum generated during the operation of the pump is variable. In certain embodiments, the pump 10 further comprises a pressure adjustment mechanism for varying the negative pressure/vacuum generated. In certain embodiments, the generation and release of the vacuum is synchronized with the tongue-imitating mechanism 50 speed and location, for imitating a baby's suckling cycle. For instance, the vacuum is activated while activating the tongue-imitating mechanism 50 until the vacuum reaches a predefined negative pressure, at which time both the tongue-imitating mechanism 50 and the vacuum generation are stopped and air is released into the space between the nipple and funnel 30, to create imitation of a baby's swallowing.

In certain embodiments, the lower manipulating mechanism 50 in any of the embodiments herein, comprises a motor 90 and one or more roller sets associated therewith, each roller set comprising one or more roller segments 150-156, such that the motor 90 rotates said one or more roller sets to constrict in a movement from front to back thereby creating a wave like motion of the lower part of said funnel 30, thereby mimicking a baby's tongue movement over the lower section of the nipple during breastfeeding. In a specific embodiment, the pump 10 is a static pump, in which the motor 90 rotates on a fixed axis. In yet another specific embodiment, the pump 10 is an active pump, in which the motor 90 rotates on a shiftable axis, i.e. the axis of the motor moves in any direction relative to the body 20.

In certain embodiments of the breastmilk pump 10 of any one of the embodiments above, the one or more roller sets comprise two or more roller segments 150-156, wherein said roller segments may change their axis-orientation relative to one another when pressed against the nipple via the funnel during a pumping cycle. Such a change in the axis-orientation enables maximum contact between the nipple and the lower part of the funnel to improve the pumping process.

In certain embodiments of the breastmilk pump 10 of any one of the embodiments above, the rotation speed of the motor 90 and roller sets is variable according to the progress of the pumping process, namely increase or decrease the rotation speed in order to increase or decrease, respectively, the pumping of the milk as the pumping process progresses. In certain embodiments, the rotation speed is automatically controlled by said microcomputer.

In certain embodiments, the different motors in the pump of the invention, e.g. the roller motor 90, the vacuum motor, etc., are dynamic motors in which the power is adjustable from 0 to max, which enables controlling and tuning their activity and strength of activation according to need during the pumping process. Such motors are also called (PWN) motors.

In certain embodiments of the breastmilk pump 10 of any one of the embodiments above, the funnel 30 further comprises an air inlet associated with a valve 27 that is designed to enable passage of air into the space between the funnel and nipple, such that when the vacuum generation is stopped or decreased and air is pumped/pressed/sucked into said space via said valve 27, the funnel 30 loosens its embracing of the nipple to imitate a baby's swallowing mechanism, optionally in correlation with the stopping of the lower manipulating mechanism 50 that imitates a baby's tongue sucking mechanism. In specific embodiments thereof, the microcomputer further controls the air inlet's valve 27 for enabling entrance of air into the pump and releasing/reliving the vacuum therein.

In certain embodiments of the breastmilk pump 10 of any one of the embodiments above, the lower manipulating mechanism 50 and said vacuum unit create a synergistic effect to improve the pumping process. In certain embodiments, the synergistic effect is obtained by mimicking a baby's suckling cycle, i.e. when vacuum is generated between the nipple and funnel, the lower manipulating mechanism 50 is activated, thereby imitating a baby's sucking and facilitating breastmilk pumping; and when the vacuum reaches a predefined negative pressure value, and/or a certain amount of milk is extracted, both the vacuum generating unit and the lower manipulating mechanism 50 stop working, and air is allowed to enter into the space between the funnel and nipple via the valve 27, thereby imitating a baby's swallowing. This imitation of the suckling cycle improves the pumping process, increases milk flow and production, and reduces undesired affects such as abrasion and pressure on the nipple. In certain embodiments, the synergistic effect is obtained by various synchronization between the different functions of the breastmilk pump 10, such as between the vacuum intensity and rotation speed of the tongue-imitating mechanism during the pumping process; the intensity and speed of the tongue-imitating mechanism, and optionally the vacuum intensity and/or vacuum cycle(s) and or the location of the upper movable element 42; etc.

In certain embodiments of the breastmilk pump 10 of any one of the embodiments above, the pump 10 is an electric breastmilk pump.

In certain embodiments of the breastmilk pump 10 of any one of the embodiments above, the pump 10 further comprises an integral power source.

In certain embodiments of the breastmilk pump 10 of any one of the embodiments above, the pump 10 further comprises further an integral screen or touchscreen for displaying and optionally for operating the breastmilk pump 10.

The present invention further provides a breastmilk pump system for pumping breastmilk, comprising: (1) a minimal breastmilk pump unit 100 designed to be attached to the breast and nipple, said unit 100 comprising: (a) a body 20; (b) a funnel 30 having a distal end 26 and a proximal end 24; and (c) a lower manipulating mechanism 50; wherein: (i) said funnel 30 is designed to fit into said body 20; (ii) said funnel's proximal end 24 has a conic shape designed to embrace a nipple, and is made of a flexible material; and (iii) said lower manipulating mechanism 50 is a tongue-imitating mechanism designed to mimic a baby's tongue movement during breastfeeding, and (2) a remote unit 101 for collecting the pumped breastmilk, said unit 101 comprising a breastmilk container, wherein said funnel 30 is fluidly connected to said breastmilk container.

In certain embodiments, the present invention provides a breastmilk pump system for pumping breastmilk from the breast of a mother, comprising: (1) a minimal breastmilk pump unit 100 designed to be attached to the breast and nipple, said unit 100 comprising: (a) a body 20; (b) a funnel 30 having a distal end 26 and a proximal end 24; and (c) a lower manipulating mechanism 50; wherein: (i) said funnel 30 is designed to fit into said body 20; (ii) said funnel's proximal end 24 has a conic shape designed to embrace a nipple, and is made of a flexible material; and (iii) said lower manipulating mechanism 50 is a tongue-imitating mechanism designed to mimic a baby's tongue movement over the breast/nipple during breastfeeding; (2) a remote unit 101 for collecting the pumped breastmilk, said unit 101 comprising: (a) a detachable breastmilk container; and a vacuum unit associated with said funnel 30 and designed to generate negative pressure (vacuum) in the pump 10 and between the funnel 30 and the breast; (3) at least one sensor designed for sensing/measuring at least one of: location of the lower manipulating mechanism 50, rotation (speed and number) of the lower manipulating mechanism 50, negative pressure intensity, distance between the funnel and the breast; milk flow; and the location of the upper movable element 42, or any combination thereof; and (4) a microcomputer comprising a processor coupled to a memory, and interfaces wherein the memory contains instructions that, when executed by the processor, cause the processor to activate/deactivate said vacuum unit and said lower manipulating mechanism 50 in a cyclic manner, and optionally change the vacuum intensity, lower manipulating mechanism 50 speed and position thereof, based on (i) data (continuously) received from said at least one sensor; and (ii) predefined parameters stored in said memory, wherein said funnel 30 is fluidly connected to said breastmilk container.

In specific embodiments of the breastmilk pump system of the embodiments above, the remote unit 101 comprises only said detachable breastmilk container.

In certain embodiments of the breastmilk pump system of the embodiments above, the system further comprises a screen or a touchscreen associated therewith for displaying and optionally for operating thereof.

In certain embodiments of the breastmilk pump system of the embodiments above, the funnel 30 further comprises an air inlet associated with a valve 27, and wherein said microcomputer further controls the air inlet's valve 27 for enabling entrance of air into the pump and releasing/reliving the vacuum therein.

In certain embodiments of the breastmilk pump system of any one of the embodiments above, the remote unit 101 further comprises a power source and/or a vacuum unit for generating a vacuum between the nipple and the funnel.

In certain embodiments of the breastmilk pump system of any one of the embodiments above, the remote unit 101 further comprises operation buttons, e.g. for activating the system and controlling the pumping process, e.g. the pumping speed and vacuum intensity, the location of the lower manipulating mechanism 50 and optionally the upper part of the funnel, the pumping cycle, the operation speed and cycle of the lower manipulating mechanism 50, or any combination thereof.

In certain embodiments of the breastmilk pump system of any one of the embodiments above, the remote unit 101 further comprises a microcomputer comprising a processor and a memory as described hereinabove.

In certain embodiments of the breastmilk pump system of any one of the embodiments above, the remote unit 101 comprises: a power source, a vacuum unit, a microcomputer comprising a processor and a memory, a breastmilk container, operation buttons, and optionally a power source.

In certain embodiments, the present invention provides a breastmilk pump system according to any one of the embodiments above, further comprising a second minimal breastmilk pump unit 100 for enabling the user to pump breastmilk simultaneously from both breasts.

In certain embodiments of the breastmilk pump system of any one of the embodiments above, the remote unit 101 comprises only the breastmilk container, which is fluidly connected to the minimal breastmilk pump unit 100. In such embodiments, all other components of the system are located in the minimal breastmilk pump unit 100, and/or in a nearby remote controller associated therewith.

In certain embodiments, microcomputer of the pump or system according to any one of the embodiments above is designed to record pumping sequences, which breast was last pumped, specific user preferences, including vacuum intensity, speed, location of the lower manipulating mechanism 50, etc. as a function of time. In yet other embodiments, the microcomputer is designed to collect statistics of all parameters and optionally transfer same to a remote microcomputer, such as a smartphone for analysis and optionally reporting to the user or a healthcare personal according to need.

The present invention may be understood by reference to the following detailed description when read with regard to the accompanying drawings, in which FIGS. 1-9 illustrate examples of breastmilk pumps 10 and components thereof according to different embodiments of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Any reference in the specification to a system should be applied mutatis mutandis to a method that can be executed by the system. Any reference in the specification to a method should be applied mutatis mutandis to a system capable of executing the method.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Specific, non-limiting, embodiments of breastmilk pumps 10 according to the invention will now be illustrated with reference to the accompanying figures.

FIG. 1 illustrates a breastmilk pump 10 showing: (a) a body 20 defining an inner space and designed to hold (b) a flexible interfacing element referred to herein as a funnel 30, wherein said funnel 30 has a proximal end 24 that is designed to come in direct contact with the breast and nipple, and serving as an inlet, and a distal end 26 designed to deliver the pumped milk to its destination, and servings as an outlet;

In certain embodiments, the pump 10 is an electric pump, having a power switch 120. In specific embodiments, the electric pump 10 is designed to be connected to the main power grid. In alternative specific embodiments, the electric pump 10 is designed to be powered by batteries, optionally rechargeable, in which case it might further comprise an integral power source, optionally rechargeable.

As can be seen in FIG. 1C, in certain embodiments the breastmilk pump 10 comprises: (i) an upper manipulating mechanism 40 for affecting a shape of an upper part of the funnel 30. The upper manipulating mechanism 40 may include an upper movable element 42 that may be curved, flat, or shaped as a palate, and may be moved between different positions thereby changing the shape of the upper part of the funnel 30. The upper movable element 42 may be moved under the control of a control knob 44 that may extend outside the body 20 and may be controlled by a user; and (ii) a lower manipulating mechanism 50 for affecting a shape of a lower part of the funnel. As shown in the figures, the lower manipulating mechanism 50 may include one or more roller sets comprising one or more roller segments 150-156 that are moved in a repetitive manner during the pumping cycles in order to repetitively squeeze milk from a breast that has (at least) its nipple inserted into the funnel 30. In certain embodiments, the lower manipulating mechanism 50 further comprises an electric motor for adjusting its location relative to the body 20 thereby enabling the user to fit the funnel 30 to her breast and nipple. In such embodiments, the body further 20 comprises control units/buttons for controlling the motor and for adjusting the location of the lower manipulating mechanism 50. In certain embodiments, the upper movable element 42 further comprises an electric motor for adjusting its location relative to the body 20 thereby enabling the user to fit the funnel 30 to her breast and nipple. In such embodiments, the body further 20 comprises control units/buttons for controlling the motor and for adjusting the location of the upper movable element 42.

In certain embodiments the breastmilk pump 10 further comprises a control unit/button for controlling the vacuum unit to thereby enable control over the vacuum intensity.

Figure 6A:
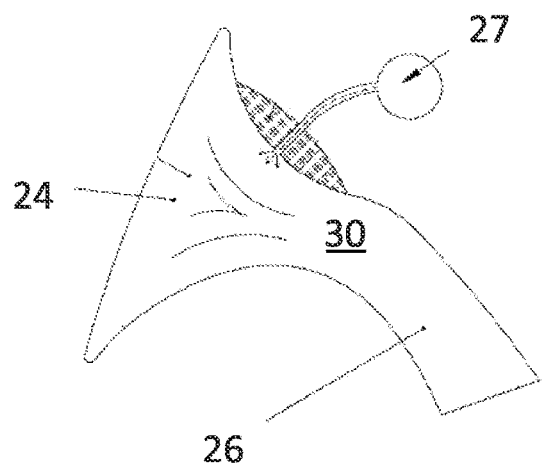
FIGS. 6A-6E illustrate the structure of the funnel according to some embodiments of the invention.
Figure 6C:
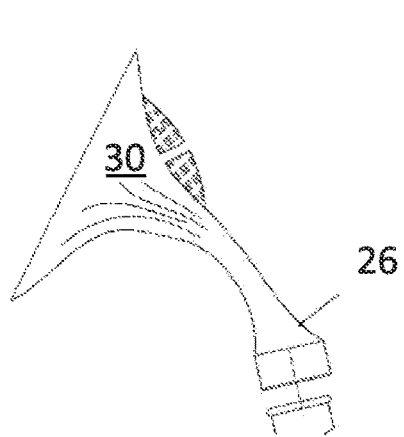
Figure 6B:
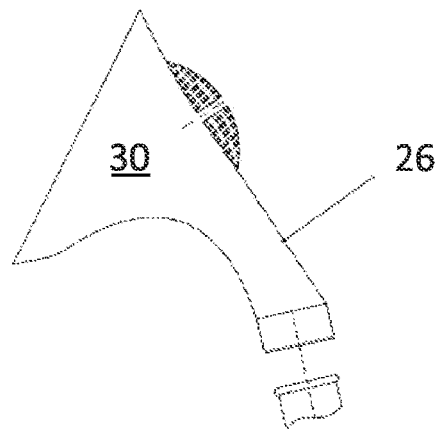

FIGS. 6A-6C illustrate an embodiment of the structure of a funnel 30 according to some embodiments of the invention. In specific embodiments, the funnel is made of an elastic material, such as silicone. As can be seen in the figures, the funnel 30 has a conic proximal end 24, to embrace the nipple. In addition, the elasticity of the funnel 30 enables it to modify its form due and/or in response to the vacuum generated and the operation of the tongue simulating device, to best fit the nipple and obtain maximal contact therewith thus increasing pumping efficiency and comfort for the mother. In certain embodiments, the funnel's proximal end modifies its shape to imitate the baby's mouth, and is adjustable according to the changing geometry of the baby's mouth during growth. Such elasticity also mimics the baby's mouth and elicits a palate. The funnel 30 also has a distal end 26 that resembles the baby's throat, and designed to be fluidly connected to a container for collecting the pumped breastmilk. In certain embodiments, the funnel 30 further comprises an air inlet fluidly connected to a valve 27, such as a one-way valve or an electric valve, for enabling passage of air inwardly and/or outwardly to mimic the swallowing effect.

Figures 6D, 6E:
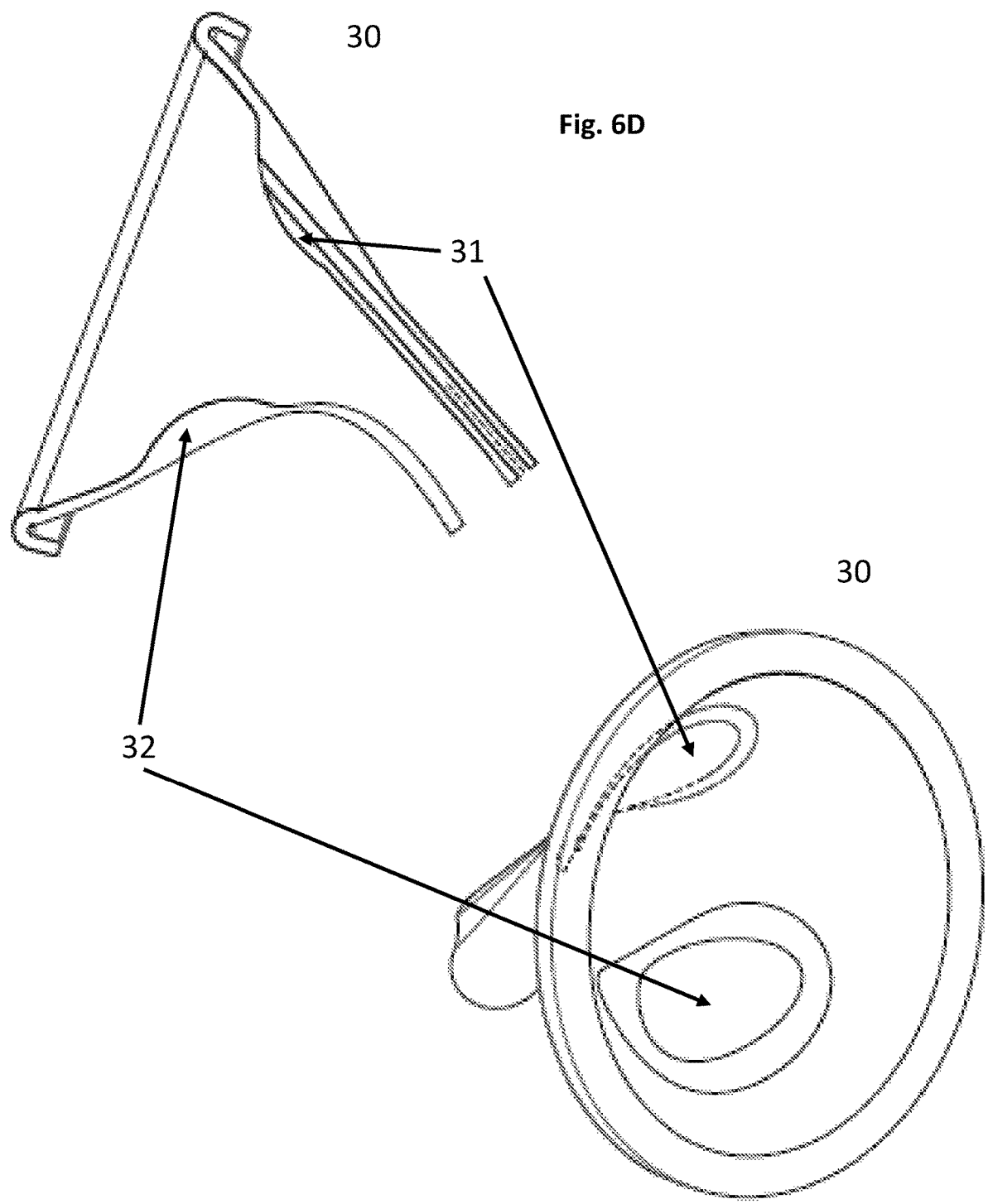

In certain embodiments, and as illustrated in FIGS. 6D-6E, the thickness and flexibility of the funnel 30 varies between different areas thereof. In certain embodiments, this variability enables the funnel 30 to collapse differently in various areas to thereby perfectly embrace the nipple/breast during the pumping process while creating optimal contact and pressure between the upper part of the funnel (imitating the palate) and the lower part of the funnel (imitating the tongue). As seen in FIG. 6D (side-cross view) and in FIG. 6E (front D view), the funnel 30 may comprise thicker areas imitating the baby's upper palate area 31 as well as the tongue area 32. In certain embodiments, the imitation of a baby's tongue movement is obtained by a thicker area at the bottom of the funnel 30 which is moved in a forward wavelike motion via the lower manipulating mechanism 50, that is located either within said thicker area or underneath it. In addition, thinner regions of the funnel 30 improves the ability of these (and other areas therein) to fold and collapse to better engulf the breast/nipple. In certain embodiments, this variability creates variable pressure points between the funnel and the breast/nipple throughout the entire funnel surface coming in touch with the breast/nipple.

In certain embodiments, the end of the funnel proximal end 24 is designed to cover the edge of the body's 20 opening (see e.g. FIG. 1C) after insertion/placement therein.

As illustrated in FIG. 1C (arrows at the bottom of the pump 10), in certain embodiments, the lower manipulating mechanism 50 can be moved in relation to the body 20/housing. The movement may be a linear movement towards the front and back, i.e. towards the inlet 24 or away therefrom. Any other movements, such as up & down, left & right, and diagonally, may also be used. In certain embodiment, the movement of the lower manipulating mechanism 50 changes the pumping process and may be set by the user to increase or decrease the pumping efficiency, i.e. by better adjusting the fitting of the funnel 30 to the nipple and breast, and by better fitting the tongue-imitation generated by the lower manipulating mechanism 50 to the shape and structure of the nipple and breast of the user. In certain embodiments, the pumping process is further improved by simultaneously controlling the pumping speed, i.e. increasing the rotation speed of the lower manipulating mechanism 50 to increase the number of contacts between the roller segments via the funnel and the nipple, and/or by controlling the pumping strength, i.e. increasing the negative pressure generated by the vacuum unit.

In certain embodiments, the lower manipulating mechanism 50 is connected to a base 130, which may move in relation to the body 20, e.g. by sliding on rails (not shown).

In certain embodiments, the movement of the control knob 44 changes the position of the upper movable element 42 that in turn modify the shape and/or location of the funnel's upper part to best fit the shape of the breast and nipple in order to reduce abrasion and improve milk production.

As seen in FIGS. 1A-1B, the control knob 44 may perform a linear movement between four positions, thus causing the upper movable element 42 to follow the movement of the control knob 44. This is merely a non-limiting example and the control knob 44 may be moved in a non-linear movement and between more or less than four positions.

In certain embodiments, the upper movable element 42 may move in parallel to the control knob 44 or may perform any movement in relation to the control knob 44.

In certain embodiments, moving the control knob 44 towards the front of the breastmilk pump 10 may (a) reduce the distance between the upper part of the funnel 30 and a bottom of the funnel 30, and/or (b) move a location of a point in which the funnel 30 is narrowed towards the nipple, and subsequently may cause the pumping process to be harder, i.e. pump harder.

The term "pumping process" as used herein refers to the breastmilk pumping procedure and includes any combination of various parameters such as pumping speed (effected by the rotation speed of the lower manipulating mechanism 50), pumping intensity (effected by the vacuum strength), milk flow/production, pressure and negative-pressure applied on the nipple and breast, location of the lower manipulating mechanism 50 relative to the body 20, duration of the air and vacuum release, etc., all of which dynamically vary during the pumping as a function of time.

In certain embodiments, the control knob 44 may be moved several times (or none) during the pumping session. In other embodiments, the control knob 44 is moved electronically, e.g. by the microcomputer.

In alternative embodiments, the upper movable element 42 may be moved by a motor, optionally operable by the control know 44.

In certain embodiments, the lower manipulating mechanism 50 comprises one or more roller sets comprising one or more roller segments 150-156 that may be moved manually or by a dedicated motor 90. FIGS. 4A-4F illustrate a motor 90 that rotate such roller sets. For brevity of explanation, the following description will refer to a lower manipulating mechanism 50 that includes an electric motor 90. In certain embodiments, the lower manipulating mechanism 50 and the upper movable element 42 are automatically adjusted for best fit the nipple and breast by using data obtained from sensors that measure proximity of the funnel to the nipple and breast, the pressure applied thereon during pumping, the amount and flow speed of the milk, etc.

In certain embodiments, the movement of the one or more roller sets is aimed to mimic the movement of a tongue and the suckling of milk by a baby. Thus, multiple sucklings are mimicked by multiple rotations of the one or more roller sets.

In certain embodiments, the one or more roller sets comprising said one or more roller segments 150-156 may be rotated about an axis of rotation 80. In certain embodiments, the axis of rotation 80 is normal to a longitudinal axis of the body 20. In alternative embodiments, any other orientation between the axis of rotation 80 and the body 20 exist.

As seen in FIGS. 4A-4F, in certain embodiments, the one or more roller sets are 1, 2, 3, 4, 5, 6 or more sets comprising one or more roller segments. In further other embodiments, each roller set of the one or more roller sets includes/comprised-of one or more roller segments 150-156, namely 1, 2, 3, 4 or more roller segments. In specific embodiments, the one or more roller sets are 2-4 sets, each includes/comprised of two roller segments. In certain embodiments, the number of roller sets is any positive integer, such as two, three or four sets.

In certain embodiments, the one or more roller sets comprising one or more roller segments 150-156 include roller segments that are, during a part of a pumping cycle, oriented in relation to the axis of rotation 80. In specific embodiments, when the roller set senses the nipple through the funnel 30, the roller segments thereof change their orientation in relation to one another (i.e. no longer oriented in relation to the axis of rotation 80) to thereby surround the nipple. This design, also referred to as a motion angle of the roller segments, better mimics the tongue-like mechanism of a sucking baby, in which the tongue engulfs the nipple, and thereby eases the pumping process and increases the efficiency of the pumping process. In certain embodiments, after each roller set leaves the nipple (rolls away from), it may return to a default position when the set does not sense the nipple through the funnel 30, e.g., oriented in relation to the axis of rotation 80.

In certain embodiments, and as illustrated in FIGS. 4E-4F, the motion angle between the roller segments is flexible and is designed to enable the roller segments to snugly fit all nipples' sizes and shapes. The flexibility of the motion angle enables autonomous real-time modification of the angle between the roller segments during the pumping session, such that when the breast is depleted and/or the nipple changes its stiffness, the angle between the roller segments is adjusted accordingly to maintain the pumping process at its highest efficiency.

In specific embodiments, the roller sets may be constantly positioned in an oriented position and not just when the set senses the nipple through the funnel 30.

In certain embodiments, when the one or more roller sets include two roller segments that may change their orientation relative to one another during a pumping cycle, one of the roller segments is static during the entire pumping cycle, whereas the other roller segment changes its orientation relative thereto. In alternative embodiments, both roller segments change their orientation. In yet other alternative embodiments, when the one or more roller sets include three or more roller segments that may change their orientation relative to one another during a pumping cycle, at least one of the roller segments is static during the entire pumping cycle, whereas the other roller segments change their orientation relative thereto.

In certain embodiments, the roller sets comprising one or more roller segments 150-156 are flexible or rigid.

In certain embodiments, the roller segments 150-156 have a cylindrical shape. In alternative embodiments, they have any other shape, such as conic-shape. In certain embodiments, the roller segments may be rigid conus-shaped, such as to create a groove-like structure into which the nipple enters during each pumping cycle.

In certain embodiments, the rotation speed or any other movement of the roller sets may be changed, either by the user or in any other manner, e.g. automatically in response to pumping progress: for instance if the pump 10 identifies that the flow of breastmilk is reduced, the pump 10 may increase or decrease the rotation speed of the roller sets and/or modify their orientation one relative to the other in order to increase the flow of breastmilk.

In certain embodiments, each roller set is positioned between holding elements that may be rotated by a motor 90 and/or any gear mechanism.

In certain embodiments, and as illustrated, e.g. in FIG. 4, multiple pairs of arms 110,112, 114,116 designed to hold the roller sets, extend outwards from an axis of rotation 80 and are rotated about the axis of rotation 80.

In certain embodiments, a set of lower interfacing elements is positioned between each pair of arms 110,112,114, 116 and is mechanically coupled to at least one of the pair of arms. In certain embodiments, the pair of arms 110,112, 114,116 include mechanical interfacing elements and/or is coupled to mechanical interfacing elements that carry (or are otherwise attached to) the roller sets. For example, each arm of a pair of arms a may include an axis (flexible or non-flexible) on which a roller is positioned. In another example, a single axis (flexible or non-flexible) may be connected to one of the arms, and the set may be connected to the axis or rotate about the axis.

In certain embodiments, the design of the breastmilk pump 10 of any one of the above embodiments provides an optimal pumping process that is highly efficient and pleasant to the mother.

In certain embodiments, the funnel 30 is made of silicone or other flexible material that can also be easily washed, sanitized and/or sterilized.

As illustrated in FIG. 5, in certain embodiments the funnel 30 may be dismantled from the body 20, e.g. for cleaning, replacement or disposed of. Accordingly, in specific embodiments, the funnel 30 is replaceable (or not) and/or disposable (or not).

In certain embodiments, the front part of the body 20 (and the funnel 30) have a concave shape or any other shape that may fit a breast. In specific embodiments, the shape of the front part of the body 20 (and the funnel 30) is adjustable in order to best fit the specific nipple of the user.

In certain embodiments, the milk pump 10 of any one of the embodiments disclosed herein, further comprises a vacuum unit designed to create negative pressure to assist in pumping the breastmilk and forwarding same from the inlet 24 to the outlet 26 of the funnel and eventually into a milk container.

FIG. 7B is a diagram illustrating the mechanism of action of the vacuum unit. In certain embodiments, the vacuum unit improves the pumping process and efficiency and thereby reduces the need for intense pumping. The reduction of intense pumping in turn assists in reducing the vibration and loudness of the breastmilk pump of the invention. Accordingly, in certain embodiments, the breastmilk pump 10 according to the any one of the embodiments herein further comprises a vacuum unit that improves pumping process and efficiency thereof, reduces vibration and loudness, and aids in the mimicking of the baby's sucking.

Figure 8A:
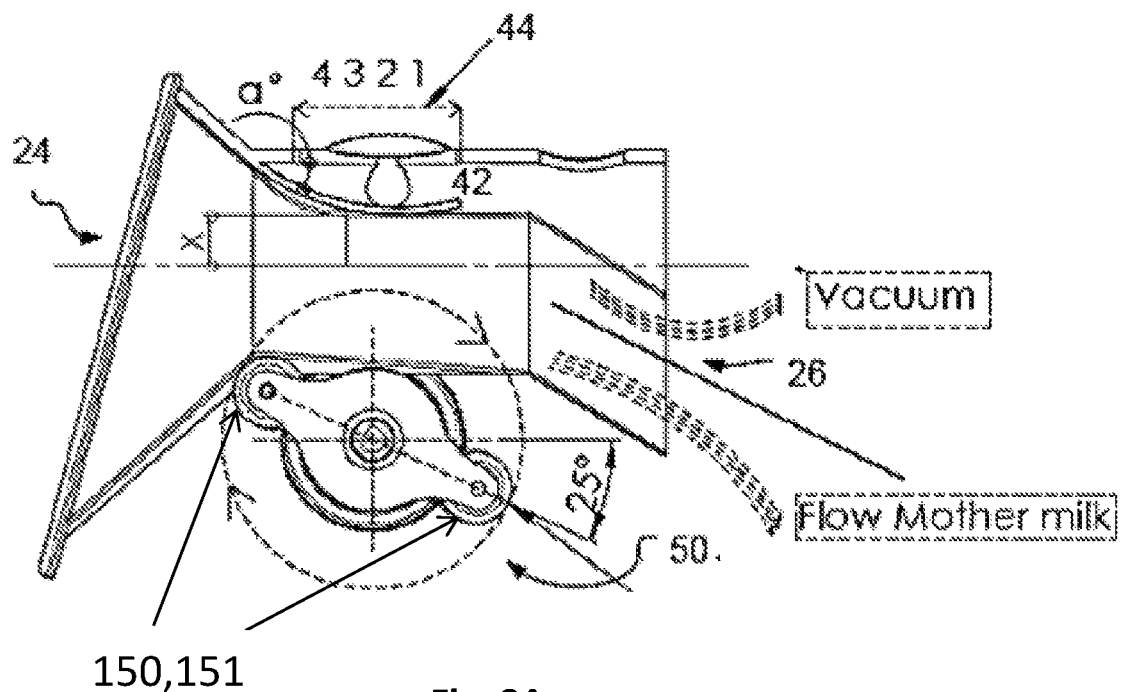
FIGS. 8A-8B illustrate the tongue-like motion and vacuum imitation mechanisms of action of the breastmilk pump according to some embodiments of the invention.
Figure 8B:
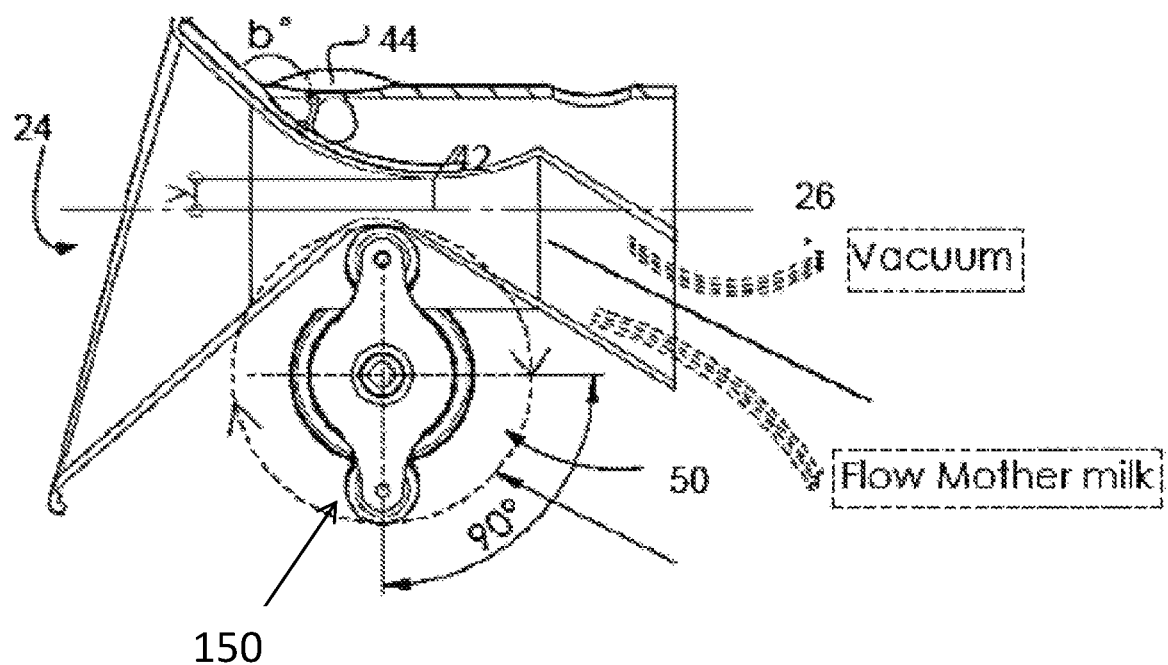

FIGS. 8A-8B illustrates how the lower manipulating mechanism 50 imitating the tongue action of a baby, and the vacuum, work in a synergy to improve the pumping process and its efficiency. Accordingly, in certain embodiments of the breastmilk pump 10 according to any one of the embodiments herein, the lower manipulating mechanism 50 together with a vacuum mechanism, such as a negative pressure pump, work in synergy to improve pumping process and efficiency thereof, and to better mimic the baby's sucking process. In certain embodiments, the synergy is obtained by mimicking a baby's suckling cycle, i.e. generating cycles of (i) negative pressure (i.e. vacuum) between the nipple and funnel, in combination with rotation of the lower manipulating mechanism 50, creating a wavelike motion of the funnel from front to back, to thereby imitate a baby's sucking and facilitating breastmilk pumping; and (ii) releasing the vacuum once it reaches a predefined negative pressure value, and or a certain amount of milk is extracted halting the lower manipulating mechanism 50, and allowing air to enter into the space between the funnel and nipple via the valve 27, to thereby imitate a baby's swallowing. This imitation of the suckling cycle improves the pumping process, increases milk flow and production, reduce the pumping time, and reduces undesired affects such as abrasion and pressure on the nipple.

Figure 8C:
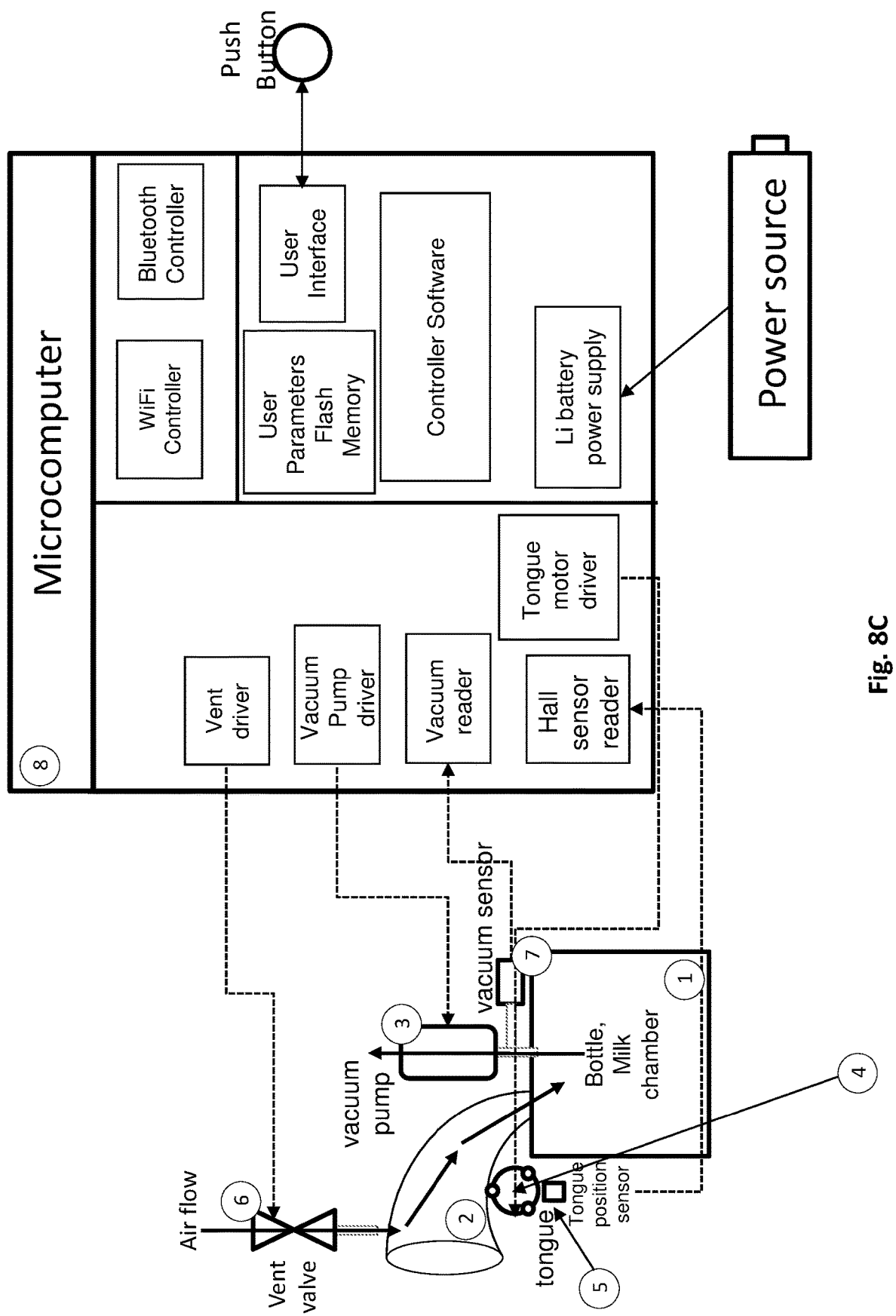
FIGS. 8C-8E illustrate the pumping process and the different role of each component in the pump of the invention.
Figure 8D:
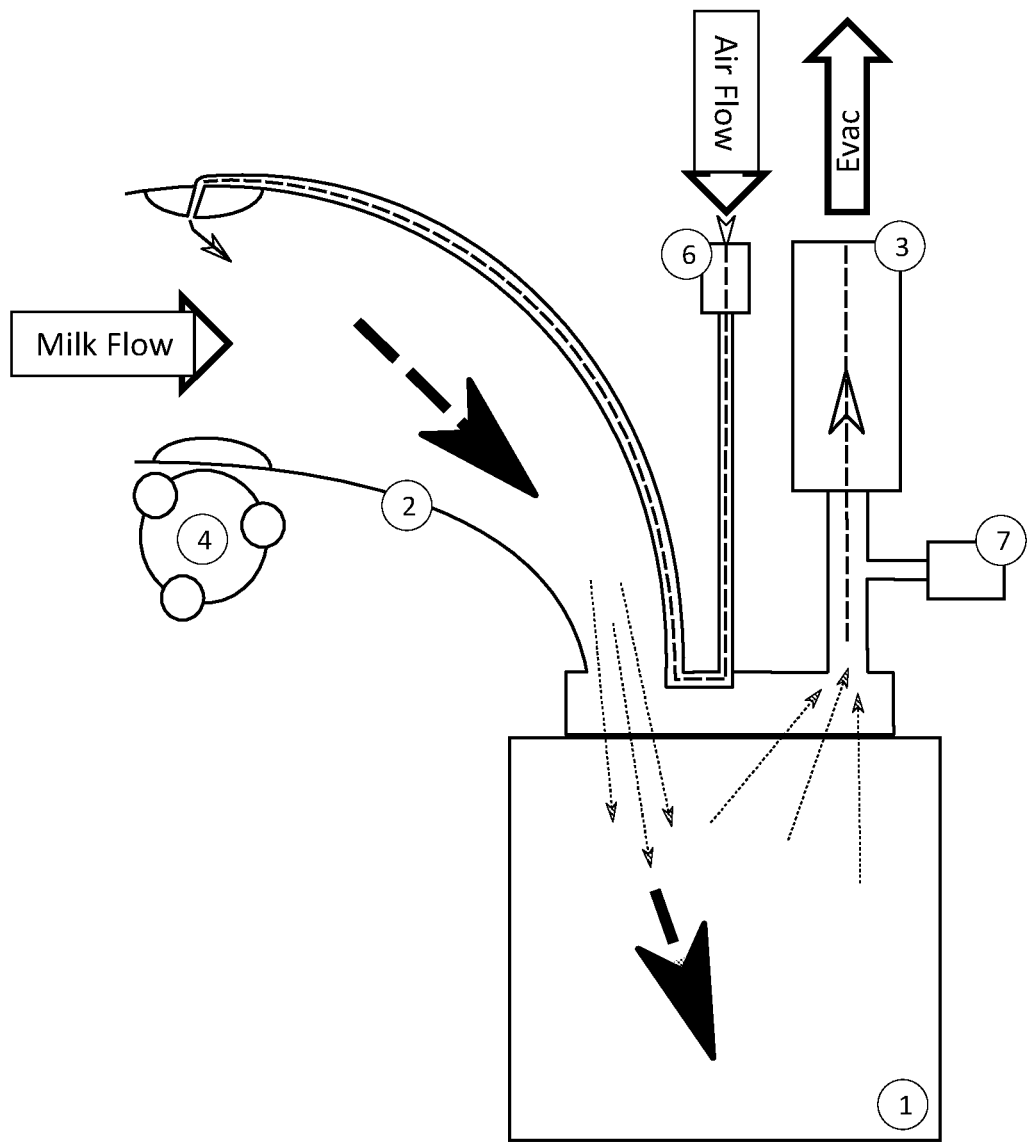
Figure 8E:
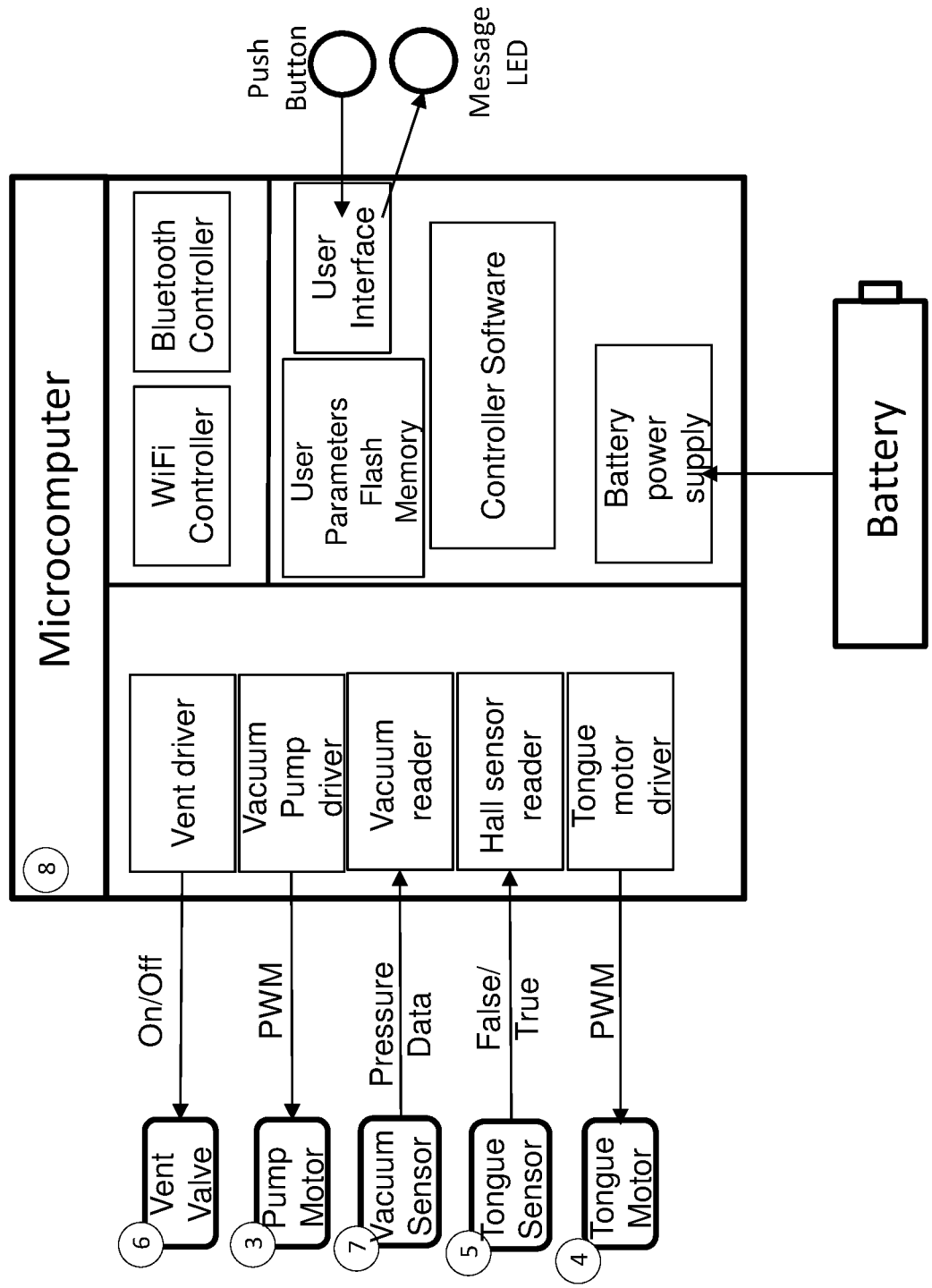

FIGS. 8C-8E illustrate exemplary embodiments of how the pump 10 and the different components therein work and synchronize during the pumping process to generate a synergy between the activity of the different components in order to create a real-life imitation of a baby's suckling process. As illustrated in FIGS. 8C-8D, the vacuum unit (3) creates a vacuum in the milk container/chamber (1) and funnel (2); the lower manipulating mechanism 50, that imitate the tongue, consists of a motor for the radial rotation (4) of the roller segments, and a "tongue" position sensor (5) for sensing the position of the roller segment and optionality a sensor for sensing the distance of the roller segments and/or the funnel from the nipple; a vent valve (6) is used to reduce/obviate the vacuum in the system (between the funnel and the nipple) and create an air flow for improving milk flow into the milk container/chamber (1); a vacuum sensor (7) is used to measure the current vacuum in the system, and together with a controller (8), the vacuum pump (3) and the vent valve (6), allows to keep up the desired pressure.

FIG. 8E illustrates that the motors are pulse width modulation (PWM) motors (3)(4) for enabling dynamic power control (from 0 to max power); a vent valve (6) having two states: open and closed (on/off); a vacuum sensor (7) for measuring real-time vacuum pressure in the pump/system; a tongue (lower manipulating mechanism 50) sensor (5) for reading the tongue position; a push button and screen (message LED) as part of a user control interface; and a controller output message for the user.

In certain embodiments, the vacuum sensor (7) is located anywhere in the milk pump 10, such as in between the funnel 30 and the breast/nipple or between the milk container and the vacuum pump (as illustrated in FIG. 8D).

Figure 2A:
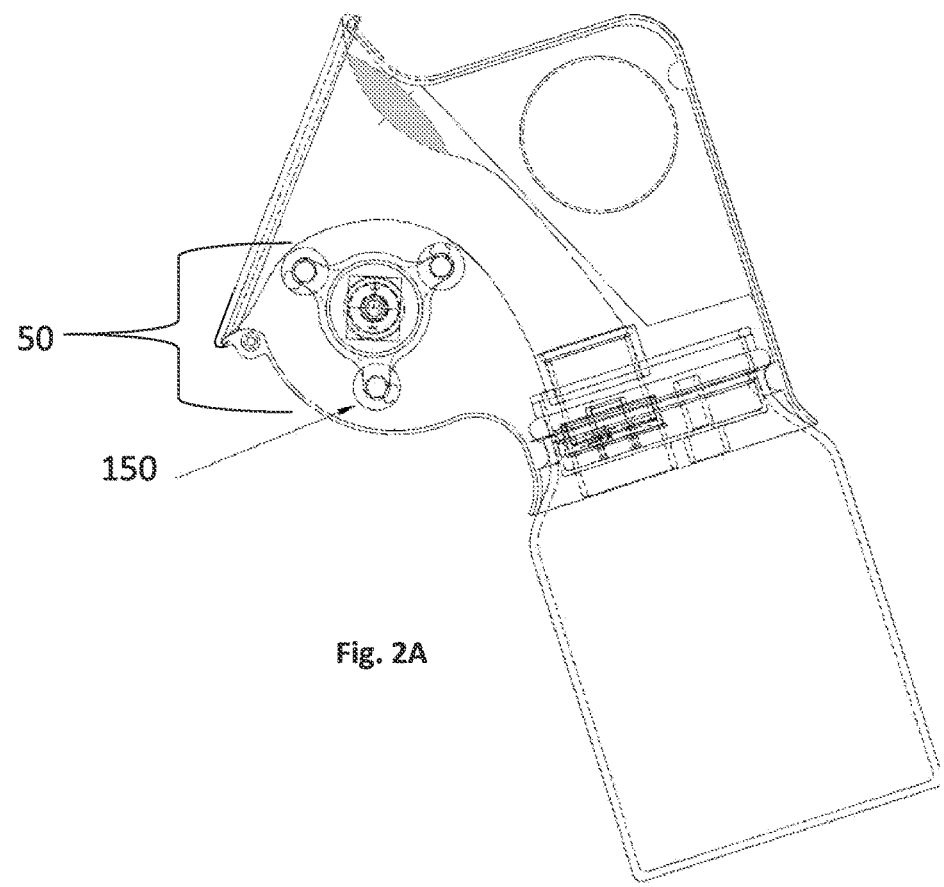
FIGS. 2A-2C are illustrations of a static breastmilk pump according to the invention.
Figure 2B:
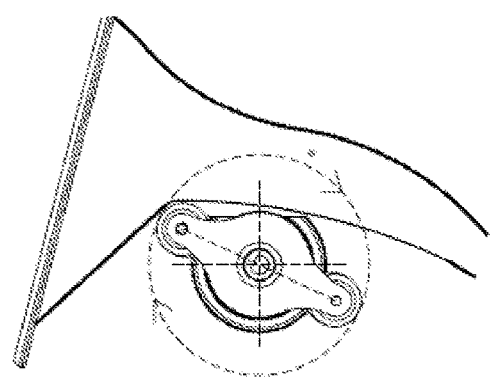
Figure 2C:
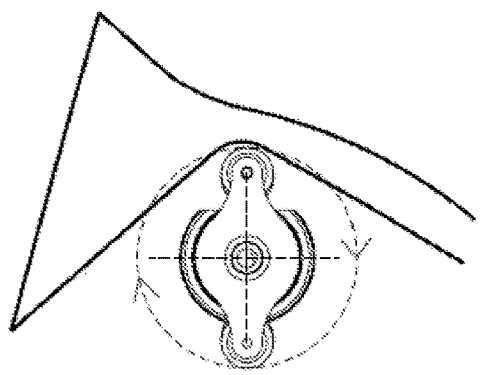

In certain embodiments, as illustrated in FIGS. 2A-2C, the milk pump 10 of any one of the embodiments above is designed as a static pump, in which the motor 90 does not move from its axis. In such a configuration, the roller sets comprising one or more roller segments 150-156 rotate around the axis in a fixed round, such that when a roller set is pushed against the lower part of the funnel, the funnel is pushed inwardly from front to back creating a wave like motion and is pressed against the nipple (and the nipple is pressed against the palate from its upper side). In such specific embodiments, the funnel 30 takes the shape of the baby's mouth cavity and elicits a palate.

In certain embodiments, as illustrated in FIGS. 3A-3C, the milk pump 10 of any one of the embodiments above is designed as an active pump, in which the motor 90 moves from its axis. Such movement of the motor 90 is achieved by pressing the roller segments of each roller set against the lower part of the body, such that in response the motor 90 is pushed upwardly against the lower part of the funnel 30, which in turn is pushed inwardly and pressed against the nipple (and the nipple is pressed against the palate that is located on the upper side of the funnel 30). In such specific embodiments, the funnel 30 takes the shape of the baby's mouth cavity and elicits a palate. As illustrated in FIG. 3C, the linear movement is defined between the minimum and maximal point of the roller sets, and the function of the funnel's trajectory defines the movement of the tongue.

FIGS. 9A-9B illustrate a breastmilk pump system, e.g., for breastmilk pumping on the go or during night. The design of the system comprise: (i) a minimal unit 100 designed to be attached to the breast and nipple in a comfortable and non-obstructive manner; and (ii) a remote unit 101 for collecting the pumped breastmilk, wherein both units are fluidly connected for breastmilk transport from the minimal unit 100 to the remote unit 101, and for passage of electricity to the electric motor(s) 90 in the minimal unit 100. Such a system enables prolong pumping of breastmilk, e.g. during the entire night, without disturbing the mother's sleep or other activities. Accordingly, in certain embodiments, the present invention provides a breastmilk pump system comprising: (i) a nipple unit that is designed to be attached to the breast and nipple and comprising a tongue-like mimicking mechanism according to any one of the embodiments above; and (ii) a remote unit 101 for collecting the pumped milk and operation buttons, and optionally a power source. In certain embodiments, the remote unit 101 further comprises a vacuum unit and a microcomputer comprising a processor and a memory.

In certain embodiments, the vacuum unit/motor, the microcomputer, the power source (if present), and the milk container are located in the remote unit 101. In alternative embodiments, the remote unit comprises only the milk container, and the other components are located either in the minimal unit 100 or spread, e.g. the microcomputer and screen/touchscreen (if present) located at a nearby controller associated with the system, and the rest within the minimal unit 100.

In certain embodiments, the breastmilk pump system of the invention is designed to be operated during the night, which the breastfeeding mother is a sleep. In such embodiments, the microcomputer is designed to activate the system automatically in cycles, e.g. every couple of minutes or hours for a predefined period of time or a cording to the identified milk flow/production.

The present invention further provides a method for pumping breastmilk, the method comprises pumping breastmilk using any one of the breastmilk pumps 10 according to the mentioned embodiments and illustrations in the specification and/or figures.

Accordingly, in certain embodiments, the present invention provides a method for pumping breastmilk, the method comprising the steps of: (a) providing a breastmilk pump 10 or a breastmilk system according to any one of the embodiments above; (b) placing the funnel 30 onto the nipple of a user; and (c) activating the pump 10 or system, thereby starting the pumping process, wherein upon activation of the breastmilk pump 10 or system, said pump or system: (i) generates a vacuum in the pump/system and between the nipple/breast and funnel 30; (ii) activates the lower manipulating mechanism 50 for imitating the tongue action of a baby; (iii) continuously monitors the vacuum strength generated between the nipple and the funnel 30; and (iv) releases the vacuum when reaching a predefined value, and deactivates the lower manipulating mechanism 50 for imitating the swallowing action of a baby; wherein the vacuum, imitation of the tongue action of a baby, and imitation of the swallowing action of a baby, are cycled synchronized to imitate a baby's suckling cycle.

In alternative certain embodiments, the present invention provides a method for pumping breastmilk, the method comprising the steps of: (a) providing a breastmilk pump 10 or a breastmilk system according to any one of the embodiments above; (b) placing the funnel 30 onto the nipple of a user; and (c) activating the pump 10 or system, thereby starting the pumping process, wherein upon activation of the breastmilk pump 10 or system, said pump or system: (i) generates a vacuum in the pump/system and between the nipple/breast and funnel 30; (ii) activates the lower manipulating mechanism 50 for imitating the tongue action of a baby; and (iii) continuously monitors the vacuum strength generated between the nipple and the funnel 30, wherein the vacuum is not released during the entire pumping process, but is maintained in various levels and its intensity is controlled by the microcomputer; wherein the vacuum, imitation of the tongue action of a baby, and imitation of the swallowing action of a baby, are cycled synchronized to imitate a baby's suckling cycle.

In certain embodiments of the method of any of the embodiments above, the vacuum intensity and/or the rolling speed of the lower manipulating mechanism 50 can vary during the pumping process, either automatically via the microcomputer or manually.

In certain embodiments of the method of any of the embodiments above, upon activation of the breastmilk pump 10 or system of any of the embodiments above, the pump or system further releases the vacuum when reaching a predefined value or when a certain amount of milk is extracted, and deactivates the lower manipulating mechanism 50, thereby imitating the swallowing action of a baby.

The present invention further provides a lower manipulating mechanism 50 that is designed to mimic the movement of a baby's tongue during breastfeeding. Such mimicking is achieved by pushing a membrane located over or on the lower manipulating mechanism 50 in a wavelike motion from front to back.

The present invention further provides a breastmilk pump comprising the lower manipulating mechanism 50 as described herein.

The present invention further provides a device for inducing/increasing breastmilk production, comprising the lower manipulating mechanism 50 as described herein.

The present invention further provides a device for inducing/increasing breastmilk production, comprising: (a) a body 20; (b) a funnel 30 having a distal end 26 and a proximal end 24; (c) a lower manipulating mechanism 50; and (d) a microcomputer comprising a processor coupled to a memory and interfaces, wherein the memory contains instructions that, when executed by the processor, cause the processor to activate/deactivate said lower manipulating mechanism 50 in a cyclic manner, and optionally the intensity, speed and position thereof, based on predefined parameters stored in said memory, wherein: (i) said funnel 30 is designed to fit into said body 20; (ii) said funnel's proximal end 24 has a conic shape designed to embrace a nipple, and is made of a flexible material; and (iii) said lower manipulating mechanism 50 is a tongue-imitating mechanism designed to mimic a baby's tongue movement by pushing the funnel 30 in a wavelike motion from front to back over the breast/nipple during breastfeeding. In specific embodiments, the device further comprises at least one sensor designed for sensing/measuring at least one of: location of the lower manipulating mechanism 50, rotation (speed and number) of the lower manipulating mechanism 50, distance between the funnel 30 and the breast; and milk flow, or any combination thereof, wherein the memory contains instructions that, when executed by the processor, cause the processor to activate/deactivate said lower manipulating mechanism 50 in a cyclic manner, and optionally the intensity, speed and position thereof, based on (i) said predefined parameters stored in said memory; and (ii) data (continuously) received from said at least one sensor. In yet other specific embodiments, the device further comprises a vacuum generating unit for withdrawal of breastmilk from the breast.

The present invention further provides a breastmilk pump comprising the device for inducing/increasing breastmilk production as described herein.

The present invention further provides a method for inducing/increasing breastmilk production in a breastfeeding mother, the method comprising the steps of: (a) providing a device for inducing/increasing breastmilk production as described hereinabove; (b) placing the funnel 30 onto the nipple of the mother; and (c) activating the device, thereby starting the induction/increasing of breastmilk production in the mother's breast, wherein upon activation of the device, said device activates the lower manipulating mechanism 50 for imitating the tongue action of a baby; and wherein the imitation of the tongue action of a baby is cycled and synchronized to imitate a baby's suckling cycle that increases oxytocin levels in the body and causes more milk to be extracted.

In the foregoing specification, the invention has been described with reference to specific examples of embodiments of the invention. It will, however, be evident that various modifications and changes may be made therein without departing from the broader spirit and scope of the invention as set forth in the appended claims.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

Furthermore, those skilled in the art will recognize that boundaries between the above described operations are merely illustrative. The multiple operations may be combined into a single operation, a single operation may be distributed into additional operations, and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The term "comprising" as used herein does not exclude the presence of other elements or steps then those listed in a claim. Furthermore, the terms "a" or "an" as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an". The same holds true for the use of definite articles.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A breastmilk pump unit for use with a breastmilk pump system configured for pumping breastmilk from a breast, said breastmilk pump system comprising a breastmilk container, said breastmilk pump unit comprising:
    a body having a front part and a back part;
    a funnel having a proximal portion associated with the front part of the body and configured to receive at least a portion of the breast, a distal portion associated with the back part of the body, and a flexible portion extending at least at a lower portion of the funnel, said funnel being configured to cooperate with a vacuum unit, so as to give rise to negative pressure within the funnel, whereby when the breast is at least partially received within the proximal portion, the breastmilk can be extracted from the breast into the funnel; the distal portion being configured to be fluidly connected to the breastmilk container, so as to deliver the breastmilk from the funnel to the breastmilk container;
    a manipulating mechanism positioned in register with said flexible portion, the manipulating mechanism is configured to move relative to the funnel to effect manipulating the flexible portion responsive to movement of the manipulating mechanism; wherein said manipulating mechanism includes:
        at least one roller segment configured to be pushed against the flexible portion; and
        a motor configured to rotate said at least one roller segment; and
    an adjustment mechanism mechanically connected to the manipulating mechanism, the adjustment mechanism configured for adjusting a location of the manipulating mechanism with respect to the funnel, the adjustment mechanism including a movable base on which the manipulating mechanism is disposed; wherein the movable base is configured to displace the manipulating mechanism, with respect to the body, at least in a direction transverse to the flexible portion of the funnel.

2. The breastmilk pump unit of claim 1, wherein said body includes a palate-imitating member, disposed above said manipulating mechanism.

3. The breastmilk pump unit of claim 1, wherein said manipulating mechanism includes:
an arm configured to hold the at least one roller segment;
wherein said motor is configured to rotate said arm together with said at least one roller segment.

4. The breastmilk pump unit of claim 1, wherein said manipulating mechanism is further configured for pushing the flexible portion of the funnel at least in a direction extending from the front part to the back part of the body.

5. The breastmilk pump unit of claim 4, wherein said manipulating mechanism is configured for pushing the flexible portion of the funnel in a wavelike motion.

6. The breastmilk pump unit of claim 1, wherein during pushing of the flexible portion of the funnel by the manipulating mechanism, the flexible portion has an uppermost position at which the flexible portion of the funnel remains disengaged from an opposite upper portion of the funnel, forming a gap therebetween.

7. The breastmilk pump unit of claim 1, wherein said funnel is configured to cooperate with said vacuum unit via said distal portion thereof.

8. The breastmilk pump unit of claim 7, wherein said vacuum unit is configured to generate variable negative pressure in a cyclic manner and said manipulating mechanism is configured to push said flexible portion in a cyclic manner, in synchronization with the cyclic manner of the variable negative pressure.

9. A breastmilk pump system configured for pumping breastmilk from a breast, the breastmilk pump system comprising:
a body having a front part and a back part;
a funnel having a proximal portion associated with the front part of the body and configured to receive at least a portion of the breast, a distal portion associated with the back part of the body, and a flexible portion extending at least at a lower portion of the funnel, said funnel being configured to cooperate with a vacuum unit, so as to give rise to negative pressure within the funnel, whereby when the breast is at least partially received within the proximal portion, the breastmilk can be extracted from the breast into the funnel; the distal portion being configured to be fluidly connected to a breastmilk container, so as to deliver the breastmilk from the funnel to the breastmilk container;
a manipulating mechanism positioned in register with said flexible portion, the manipulating mechanism is configured to move relative to the funnel to effect manipulating the flexible portion responsive to movement of the manipulating mechanism; wherein said manipulating mechanism includes:
at least one roller segment configured to be pushed against the flexible portion; and
a motor configured to rotate said at least one roller segment;
an adjustment mechanism mechanically connected to the manipulating mechanism, the adjustment mechanism configured for adjusting a location of the manipulating mechanism with respect to the funnel, the adjustment mechanism including a movable base on which the manipulating mechanism is disposed; wherein the movable base is configured to displace the manipulating mechanism, with respect to the body, at least in a direction transverse to the flexible portion of the funnel; and
a microcomputer comprising a processor coupled to a memory and an interface, wherein the memory contains instructions that, when executed by the processor, cause the processor to operate said manipulating mechanism.

10. The breastmilk pump system of claim 9, wherein said manipulating mechanism comprises:
an arm configured to hold the roller segment;
wherein said motor is configured to be operated by the processor to rotate said arm together with said at least one roller segment.

11. The breastmilk pump system of claim 9, wherein said manipulating mechanism is further configured for pushing the flexible portion at least in a direction extending from the front part to the back part.

12. The breastmilk pump system of claim 9, wherein said manipulating mechanism is configured for pushing the flexible portion in a wavelike motion.

13. The breastmilk pump system of claim 9, further comprising a connecting element configured to fluidly connect between said distal portion of the funnel and said breastmilk container, and to facilitate pressure communication between said distal portion of said funnel and said vacuum unit.

14. The breastmilk pump system of claim 13, wherein said connecting element is formed with a vacuum chamber configured to connect in the pressure communication to said vacuum unit.

15. The breastmilk pump system of claim 9, further comprising said vacuum unit.

16. The breastmilk pump system of claim 15, wherein said vacuum unit is configured to generate variable negative pressure in a cyclic manner and said manipulating mechanism is configured to push said flexible portion in a cyclic manner, in synchronization with the cyclic manner of the variable negative pressure.

17. The breastmilk pump system of claim 15, wherein said memory contains instructions that, when executed by the processor, cause the processor to operate the vacuum unit and the manipulating mechanism.

18. The breastmilk pump system of claim 9, wherein said funnel is configured to cooperate with said vacuum unit via said distal portion thereof.

* * * * *